(12) United States Patent
Nakajima et al.

(10) Patent No.: US 11,717,617 B2
(45) Date of Patent: Aug. 8, 2023

(54) INTRADERMAL NEEDLE, PACKAGING ARTICLE THEREOF, AND INJECTION DEVICE

(71) Applicant: TERUMO KABUSHIKI KAISHA, Tokyo (JP)

(72) Inventors: Kentaro Nakajima, Yamanashi (JP); Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/815,576

(22) Filed: Mar. 11, 2020

(65) Prior Publication Data
US 2020/0206432 A1    Jul. 2, 2020

Related U.S. Application Data

(63) Continuation of application No. PCT/JP2019/008622, filed on Mar. 5, 2019.

(30) Foreign Application Priority Data

Mar. 16, 2018    (JP) .................................. 2018-049357

(51) Int. Cl.
*A61M 5/32*    (2006.01)
*A61M 5/00*    (2006.01)

(52) U.S. Cl.
CPC .......... *A61M 5/3216* (2013.01); *A61M 5/002* (2013.01); *A61M 5/3286* (2013.01); *A61M 5/3293* (2013.01)

(58) Field of Classification Search
CPC .. A61M 5/3216; A61M 5/002; A61M 5/3286; A61M 5/3293; A61M 5/3202; A61M 5/32; A61M 2005/3217
See application file for complete search history.

(56) References Cited

U.S. PATENT DOCUMENTS 5,462,534 A * 10/1995 Debreczeni ......... A61M 5/3216
                                                               604/263
6,298,541 B1    10/2001 Newby et al.
(Continued)

FOREIGN PATENT DOCUMENTS

CN    105283208 A    1/2016
DE    3713754 A1    11/1988
(Continued)

OTHER PUBLICATIONS

The extended European Search Report dated Nov. 4, 2020, by the European Patent Office in corresponding European Patent Application No. 19767542.4-1122. (8 pages).
(Continued)

*Primary Examiner* — Laura A Bouchelle
(74) *Attorney, Agent, or Firm* — Buchanan Ingersoll & Rooney PC

(57) ABSTRACT

In an intradermal needle including a tubular needle that can be punctured into a living body, a packaging article, and an injection device, a pivotable protector is provided to a wide diameter part. The protector has an arm that can pivot around an axle of pivoting, and a lid. The pivoting axle part is provided to the wide diameter part, and the lid is formed to give a width smaller than a diameter of the wide diameter part. The arm keeps the lid in the open position away from the pivoting axle part and closer to an axis of the needle hub.

19 Claims, 15 Drawing Sheets

(56) References Cited

U.S. PATENT DOCUMENTS

| | | | |
|---|---|---|---|
| 7,223,258 B2 * | 5/2007 | Crawford | A61B 5/150572 604/110 |
| 2003/0199822 A1 | 10/2003 | Nehas et al. | |
| 2003/0212369 A1 | 11/2003 | Kobayashi | |
| 2007/0179451 A1 | 8/2007 | Sprinkle et al. | |
| 2012/0191042 A1 | 7/2012 | Iwase et al. | |
| 2016/0067413 A1 | 3/2016 | Madin et al. | |
| 2016/0220766 A1 | 8/2016 | Kawano et al. | |
| 2016/0303331 A1 | 10/2016 | Evans et al. | |
| 2018/0015231 A1 | 1/2018 | Kawamoto | |
| 2020/0206433 A1 | 7/2020 | Nakajima et al. | |
| 2020/0206434 A1 | 7/2020 | Nakajima et al. | |

FOREIGN PATENT DOCUMENTS

| | | |
|---|---|---|
| DE | 20 2016 1 07 000 U1 | 12/2017 |
| EP | 2 545 949 A1 | 1/2013 |
| FR | 2684004 A1 | 5/1993 |
| JP | 2000084079 A | 3/2000 |
| JP | 2005525198 A | 8/2005 |
| JP | 2016520364 A | 7/2016 |
| WO | 2004/110517 A2 | 12/2004 |
| WO | 2011040188 A1 | 4/2011 |
| WO | 2016158143 A1 | 10/2016 |

OTHER PUBLICATIONS

International Search Report (PCT/ISA/210) and translation and Written Opinion (PCT/ISA/237) dated May 21, 2019, by the Japanese Patent Office as the International Searching Authority for International Application No. PCT/JP2019/008622.

Office Action (The First Office Action) dated Jan. 4, 2022, by the State Intellectual Property Office of People's Republic of China in corresponding Chinese Patent Application No. 201980003860.1 and an English Translation of the Office Action. (16 pages).

* cited by examiner

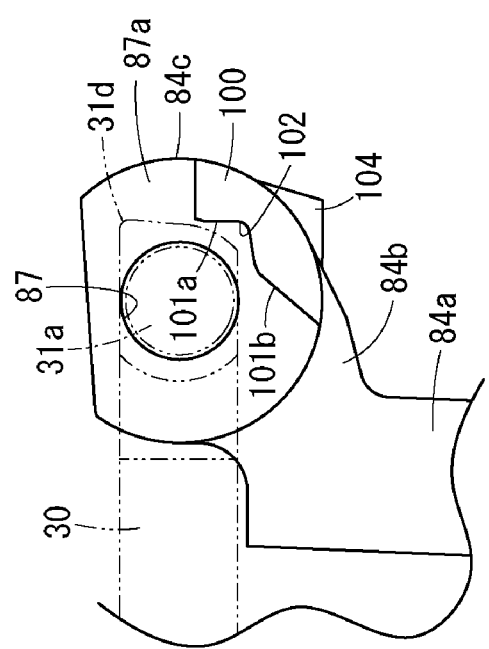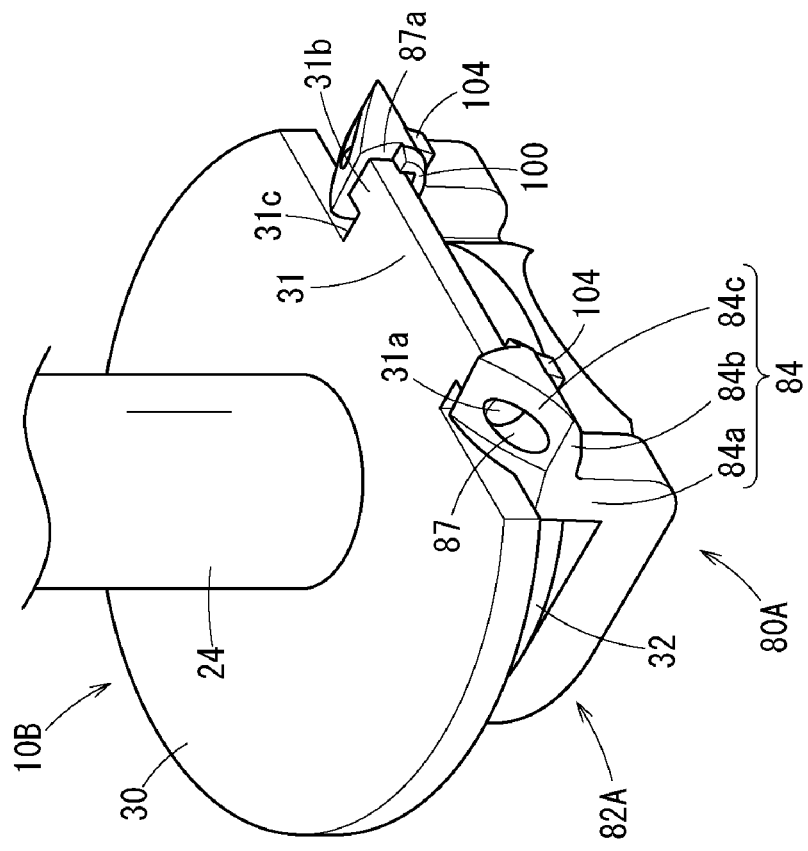

INTRADERMAL NEEDLE, PACKAGING ARTICLE THEREOF, AND INJECTION DEVICE

CROSS-REFERENCES TO RELATED APPLICATIONS

This application is a continuation of International Application No. PCT/JP2019/008622 filed on Mar. 5, 2019, which claims priority to Japanese Application No. 2018-049357 filed on Mar. 16, 2018, the entire content of both of which is incorporated herein by reference.

FIELD OF THE DISCLOSURE

This disclosure generally relates to an intradermal needle used for injecting a drug into living body, a packaging article of the intradermal needle used for injecting a drug into a living body, and an injection device.

BACKGROUND DISCUSSION

An intradermal needle has been proposed for injecting drug into an upper layer of skin. Since the intradermal needle is designed to keep a needle tip of a tubular needle within the upper layer of skin, the tubular needle has a length of protrusion of 3 mm or shorter. By virtue of such short length of protrusion of the tubular needle, the intradermal needle is less likely to cause erroneous puncture, as compared with widely-used needles for hypodermic injection. Even in the case of the intradermal needle however, the needle tip remains exposed, so that there remains a risk that the needle tip of the tubular needle may accidentally puncture the user after the drug administration or upon disposal of the injection device.

To address this problem, International Patent Application Publication No. 2016/158143 describes a technique of providing a pivotable protector to the intradermal needle. With the intradermal needle described in International Patent Application Publication No. 2016/158143, the needle tip can be prevented from accidentally puncturing the user, by pivoting the protector to cover the needle tip of the tubular needle after use.

No special attention has been paid, however, to the aforementioned intradermal needle in terms of convenience of housing in a packaging article, making the intradermal needle relatively inconvenient to handle.

SUMMARY

An intradermal needle is disclosed, which may be housed more conveniently into a packaging article, may be improved to be easier to handle, a packaging article thereof, and an injection device.

According to an aspect of the present disclosure, an intradermal needle is disclosed, which includes a tubular needle having a needle tip that can be punctured into a living body, a needle hub that supports the tubular needle, a wide diameter part that extends like a flange from the needle hub, a ring protrusion that extends to a front end side of the wide diameter part, and is formed into a cylindrical shape that surrounds a periphery of the tubular needle, and a protector pivotably attached to the wide diameter part, so as to be movable from an open position near the needle hub to a closed position where the needle tip is covered, the protector including an pivoting axle part arranged within a circular region having the same diameter as that of the wide diameter part, a lid formed to give a width smaller than a diameter of the wide diameter part, and an arm that is pivotably supported by the pivoting axle part, and keeps the lid in the open position away from the pivoting axle part and near an axis of the needle hub.

According to the aforementioned intradermal needle, the pivoting axle part is provided near the axis of the needle hub, the lid is formed to give a width smaller than the diameter of the wide diameter part, and when the protector is placed in the open position, the lid is arranged near the axis of the needle hub. Hence, when the protector is placed in the open position, the lid is housed compactly near the axis of the needle hub. This consequently makes it possible to house the intradermal needle in a small packaging article having an inner diameter comparable to the diameter of the wide diameter part.

The intradermal needle may have an open position restriction member that keeps, in the open position, a free end of the lid away from the needle hub. With such structure, when attaching a syringe to the needle hub, the free end of the lid is prevented from being brought into contact with the syringe to interfere the attachment of the syringe.

In the intradermal needle, the lid may have a closed position restriction member that restricts a stop position of the lid at the closed position of the protector, and the closed position restriction member may keep an inner face of the lid, facing to the needle tip, closer to the front end side than the ring protrusion. With this structure, the tubular needle that protrudes out of the ring protrusion may be covered with the lid.

The intradermal needle may a lock mechanism that holds the lid in the closed position. With this structure, the needle tip is prevented from being exposed, due to re-opening of the lid having been held in the closed position.

The intradermal needle may have a cutout that houses in the open position a part of the needle hub, formed at a part closer to the pivoting axle part of the lid. With this structure, the lid in the open position may be housed at the position near the axis of the needle hub, and thereby the protector may be housed compactly.

In the intradermal needle, a pair of the arms may be arranged away from each other in an axial direction of the pivoting axle part. Further in this case, the pivoting axle part may have a pair of axle pins arranged as spaced from each other in the axial direction, and the arms are engaged with the axle pins in a freely pivotable manner. With this structure, the arms will have enhanced rigidity at around the pivoting axle part, and even under force applied from directions other than the direction around the axle of pivoting, the protector will be suppressed from pivoting in wrong directions, and will therefore be prevented from unfortunately disengaging to expose the needle tip.

According to another aspect of this disclosure, a packaging article is formed to give an inner diameter nearly equal to the diameter of the wide diameter part of the intradermal needle, and houses the intradermal needle with the protector kept in the open position.

According to still another aspect of this disclosure, an injection device has the aforementioned intradermal needle, and a syringe attached to the intradermal needle in a detachable manner.

With the intradermal needle, the packaging article of the intradermal needle, and the injection device according to these aspects, convenience for housing in a relatively small packaging article and convenience for handling can be improved.

BRIEF DESCRIPTION OF THE DRAWINGS

FIG. 15A is a perspective view illustrating the intradermal needle illustrated in FIG. 13A with the protector held at a closed position.

FIG. 15B is an explanatory drawing illustrating a positional relation between the lid member and the protector mounting part in the state illustrated in FIG. 15A.

DETAILED DESCRIPTION

Set forth below with reference to the accompanying drawings is a detailed description of embodiments of an intradermal needle used for injecting a drug into living body, a packaging article of the intradermal needle used for injecting a drug into a living body, and an injection device representing examples of the inventive intradermal needle, packaging article, and injection device disclosed here.

First Embodiment

Figure 1:
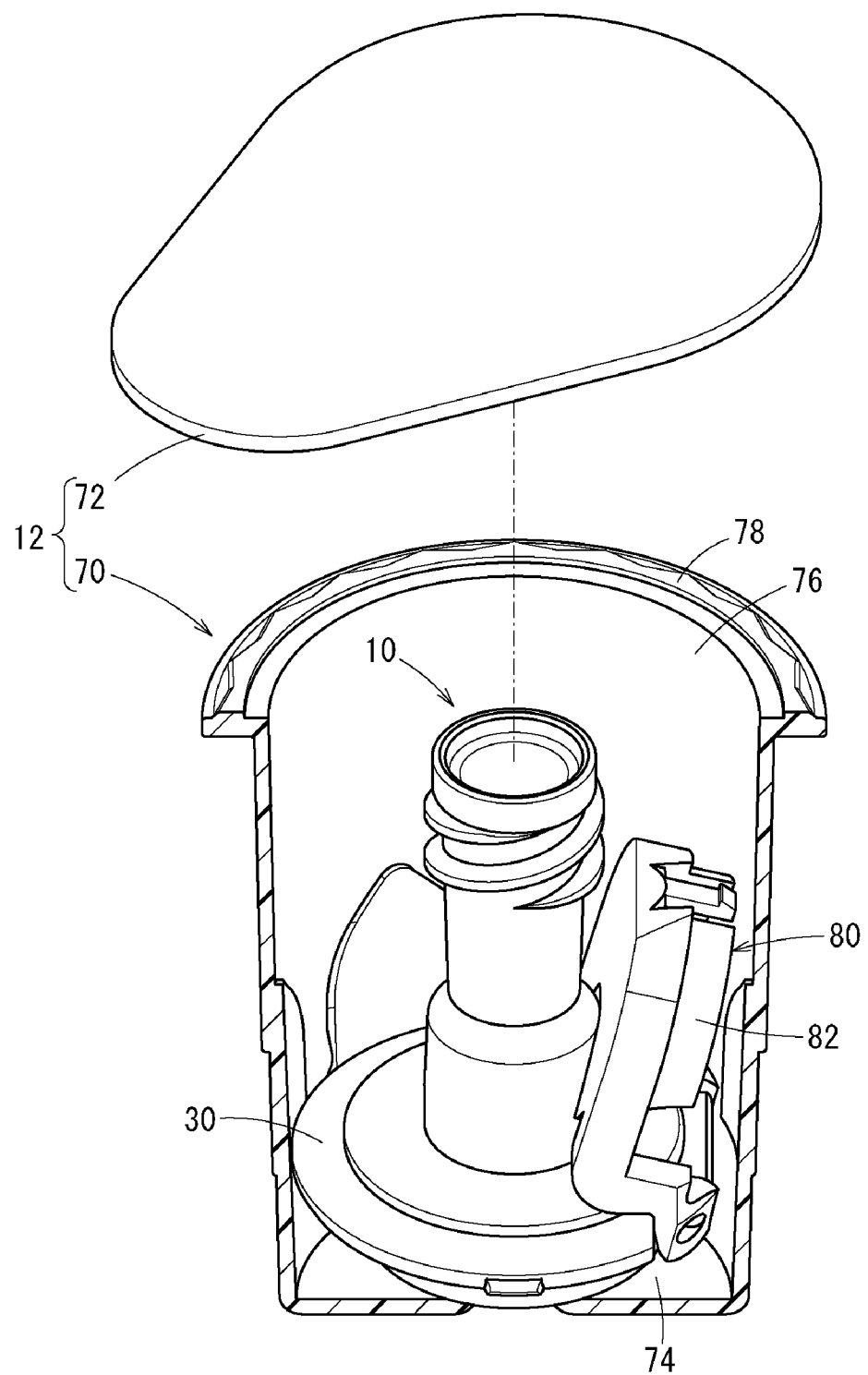
FIG. 1 is a partial cutaway perspective view illustrating a packaging article housing an intradermal needle according to a first embodiment.

An intradermal needle 10 of this embodiment is provided as a product as illustrated in FIG. 1, while being housed in a packaging article 12 that individually packages the intradermal needle (medical needle) 10. The intradermal needle 10, sealed in the packaging article 12, is kept aseptic until just before use.

The packaging article 12 includes a container 70 that houses the intradermal needle 10, and a seal member 72 that closes the container 70. When used, the seal member 72 is peeled off by the user from the container 70, thus making the intradermal needle 10 in the container 70 accessible to the user.

The container 70 possesses a cylindrical shape, with an inner space formed in the cylindrical shape, and a bottom face 74 having a circular shape whose diameter is slightly larger than the diameter (outer diameter) of the wide diameter part (enlarged diameter part) 30 of a needle hub 16. The container 70 also includes an upstanding cylinder wall 76 that extends up from the bottom face 74 in the axial direction of the intradermal needle 10. The cylindrical wall 76 is sized so that an inner diameter of the container 70 is slightly larger than the diameter (outer diameter) of the wide diameter part (enlarged diameter part) 30 of the needle hub 16. The top end of the container 70 a flange 78. The seal member 72 is attached to the flange 78.

The intradermal needle 10 is housed in the packaging article 12, with the lid member 82 of the protector 80 held in the open position. The protector 80, in the open position, is enclosed within a cylindrical region having the diameter equal to that of the wide diameter part 30, and is thus housed without interfering with the packaging article 12.

Figure 2:
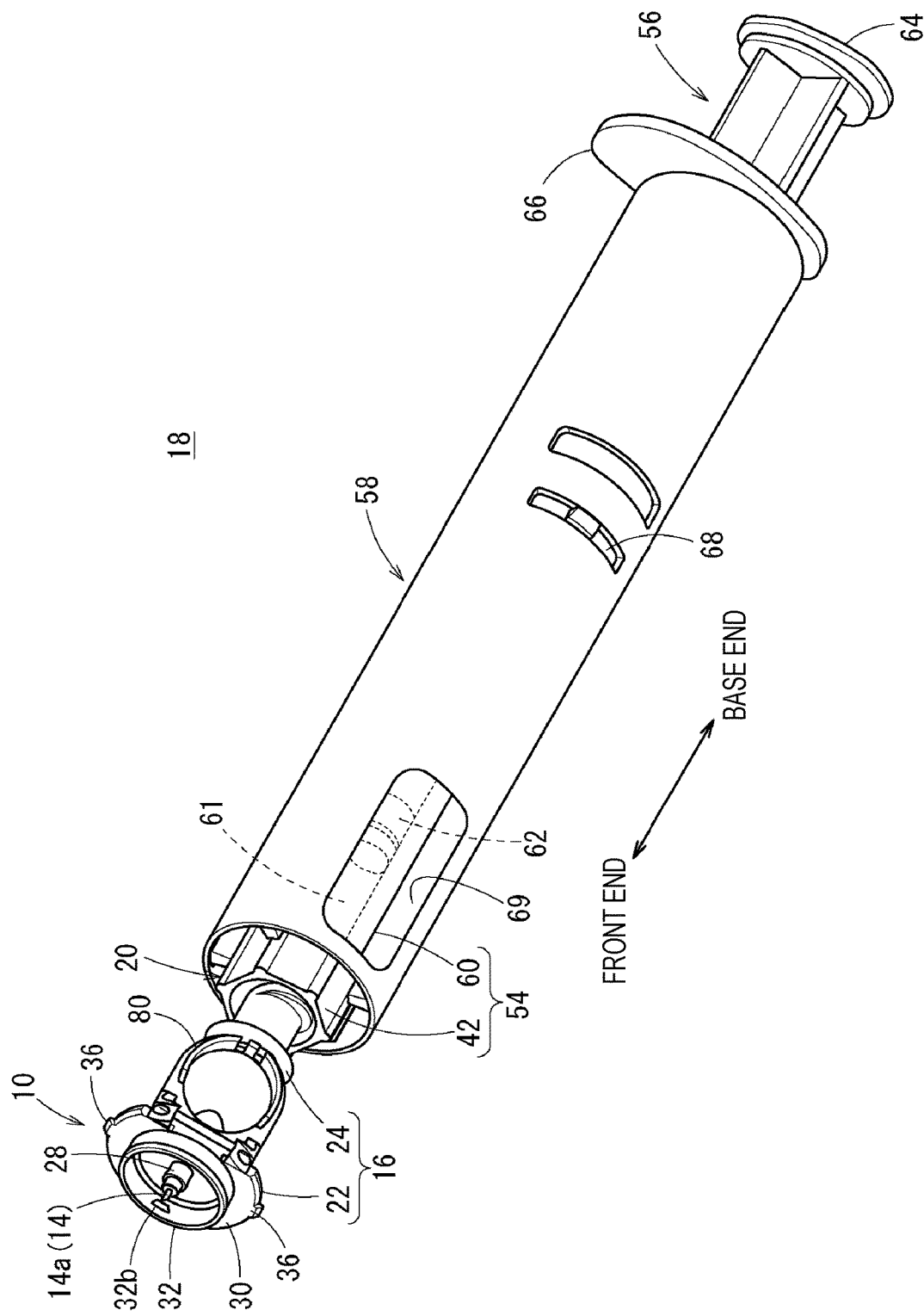
FIG. 2 is a perspective view illustrating an injection device according to the first embodiment.

The intradermal needle 10 has, as illustrated in FIG. 2, a tubular needle 14 and a needle hub 16, and composes a component of an injection device 18. When used, the intradermal needle 10 is assembled on a syringe 20, which is separately provided from the intradermal needle 10. The user attaches the syringe 20 to the intradermal needle 10 to assemble the injection device 18, and then punctures a living body with the needle tip 14a of the intradermal needle 10. Upon pressing a plunger 56 of the syringe 20 while keeping a state of puncture in the living body, a medical solution (i.e., drug) contained in the syringe 20 can be intradermally injected through the tubular needle 14 into the living body. After injection, the intradermal needle 10 is disposed, with the used tubular needle 14 covered and unexposed with the protector 80, thus making it possible to avoid accidental puncture with the tubular needle 14.

Figure 3:
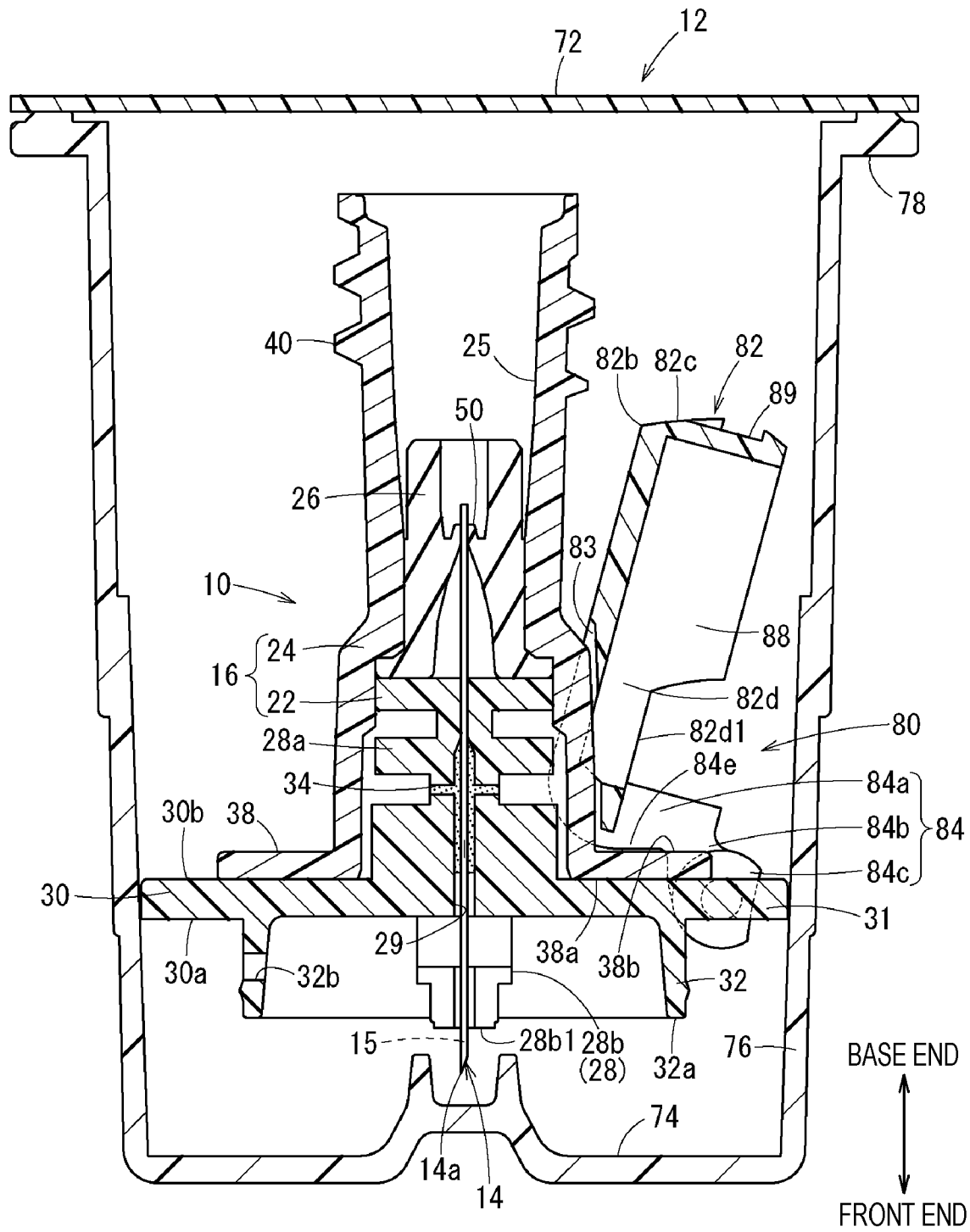
FIG. 3 is a cross-sectional view illustrating a packaging article housing the intradermal needle illustrated in FIG. 1.

The individual parts of the intradermal needle 10 will be explained below. As illustrated in FIG. 3, the tubular needle 14 of the intradermal needle 10 is a rigid hollow tube, with a needle hole 15 arranged at the axial center. The tubular needle 14 includes at the frontmost part (i.e., distal part) of the needle tip 14a a sharp blade face or pointed end. The tubular needle 14 may have a thickness not specifically limited, whose gauge number can be, for example, 26 to 33 (0.2 to 0.45 mm), and more preferably 30 to 33. Examples of materials from which the tubular needle 14 can be fabricated include stainless steel, aluminum, aluminum alloy, titanium, titanium alloy, other metals, and hard resins.

The needle hub 16 of the intradermal needle 10 includes a first member 22 to which the tubular needle 14 is fixed, and a second member 24 on which the syringe 20 to be attached to the first member 22 is assembled. Examples of materials from which the first and second members 22, 24 may be fabricated include resin materials such as polycarbonate, polypropylene, and polyethylene. The needle hub 16 can also have an elastic member 26 inside the second member 24.

The first member 22 has an axial part 28 that directly holds the tubular needle 14, the wide diameter part 30 that extends like a flange radially from the outer circumferential face of the axial part 28, and an axially extending annular or ring-shaped protrusion 32 that extends ahead of an end face 30*a* of the wide diameter part 30. The axial part 28 possesses a near cylindrical shape, and at the axial center of the axial part 28, is provided a fixing hole 29 that houses and fixes the tubular needle 14. With the tubular needle 14 positioned in the fixing hole 29, an adhesive 34 is injected to fix the tubular needle 14 and the first member 22.

The axial part 28 has a housing part 28*a* housed in the second member 24, and a protruding part 28*b* that protrudes ahead of the wide diameter part 30. The protruding part 28*b* of the axial part 28 protrudes slightly ahead of the annular or ring-shaped protrusion 32, and has an end face 28*b*1 that comes into contact with a surface of a living body. The tubular needle 14 fixed to the fixing hole 29 protrudes an appropriate amount (length of protrusion) ahead of the end face 28*b*1. For example, the length of protrusion of the tubular needle 14 is designed equivalent to the depth of dermis from the skin surface of the living body, which preferably falls in the range from approximately 0.5 mm to 3.0 mm.

The wide diameter part 30 is formed like a disk that extends from the outer circumferential face of the axial part 28 in the direction perpendicular to the center axis of the axial part 28. The wide diameter part 30 extends further beyond the annular or ring-shaped protrusion 32 in the radial direction. On the base end face or surface 30*b*, which is a face or surface on the base end side of the wide diameter part 30 (a face opposite to the end face 30*a* at which the annular ring protrusion 32 is arranged), the second member 24 is bonded. The wide diameter part 30 has on the outer circumference of the wide diameter part 30, a pair of claws 36 (see FIG. 2) that protrude outward. The pair of claws 36 are arranged on the opposite sides (180° degrees opposite position) on the outer circumference of the wide diameter part 30.

The annular or ring-shaped protrusion 32 is a part that slightly protrudes like a wall from the wide diameter part 30 towards the front end, and is configured to define a cylindrical shape that surrounds the axial part 28 while maintaining a predetermined distance in between. When using the intradermal needle 10, the entire range of an end face 32*a* of the annular or ring-shaped protrusion 32 comes into contact with the skin of the living body. The annular or ring-shaped protrusion 32 can therefore guide the injection device 18 so as to maintain the puncture posture perpendicular to the skin, and can maintain a constant depth of puncture of the tubular needle 14 into the skin.

The second member 24 is configured as a near cylindrical shape with a through-hole 25 formed along the center axis. On the front end side of the through-hole 25, the housing part 28*a* of the first member 22 is positioned, meanwhile in the middle of the through-hole 25, an elastic member 26 is housed. On the base end side of the through-hole 25, a nozzle 44 (see FIG. 7) of the syringe 20 is inserted during assemblage of the injection device 18. The inner circumferential face, on the base end side, of the through-hole 25 is tapered so as to allow surface contact with the outer circumferential face of the nozzle 44.

On the front end of the second member 24, there is provided a connecting wide diameter part 38 that extends outwards in the radial direction. The outer circumferential edge of the connecting wide diameter part 38 is inside the outer circumferential edge of the wide diameter part 30 of the first member 22. The connecting wide diameter part 38 is fixed at its end face 38*a* to the base end face or surface 30*b* of the wide diameter part 30, by an appropriate method of bonding such as vibration welding. On the outer circumferential face or surface on the base end side of the second member 24, there is provided a male screw 40 on which a female screw 47 (see FIG. 7) of the syringe 20 is screwed.

Figure 4:
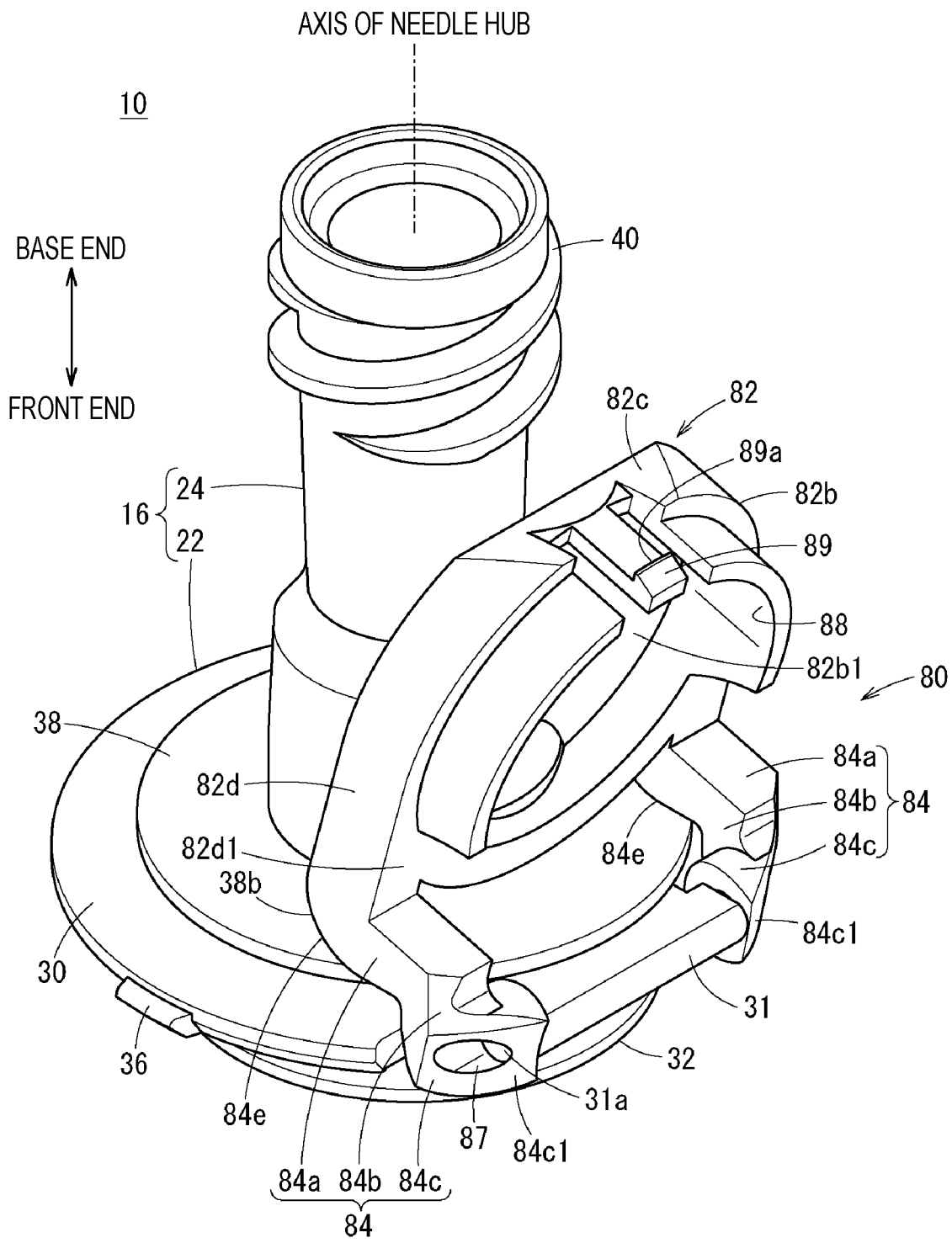
FIG. 4 is a perspective view illustrating the intradermal needle according to the first embodiment, with a protector held in the open position.
Figure 8:
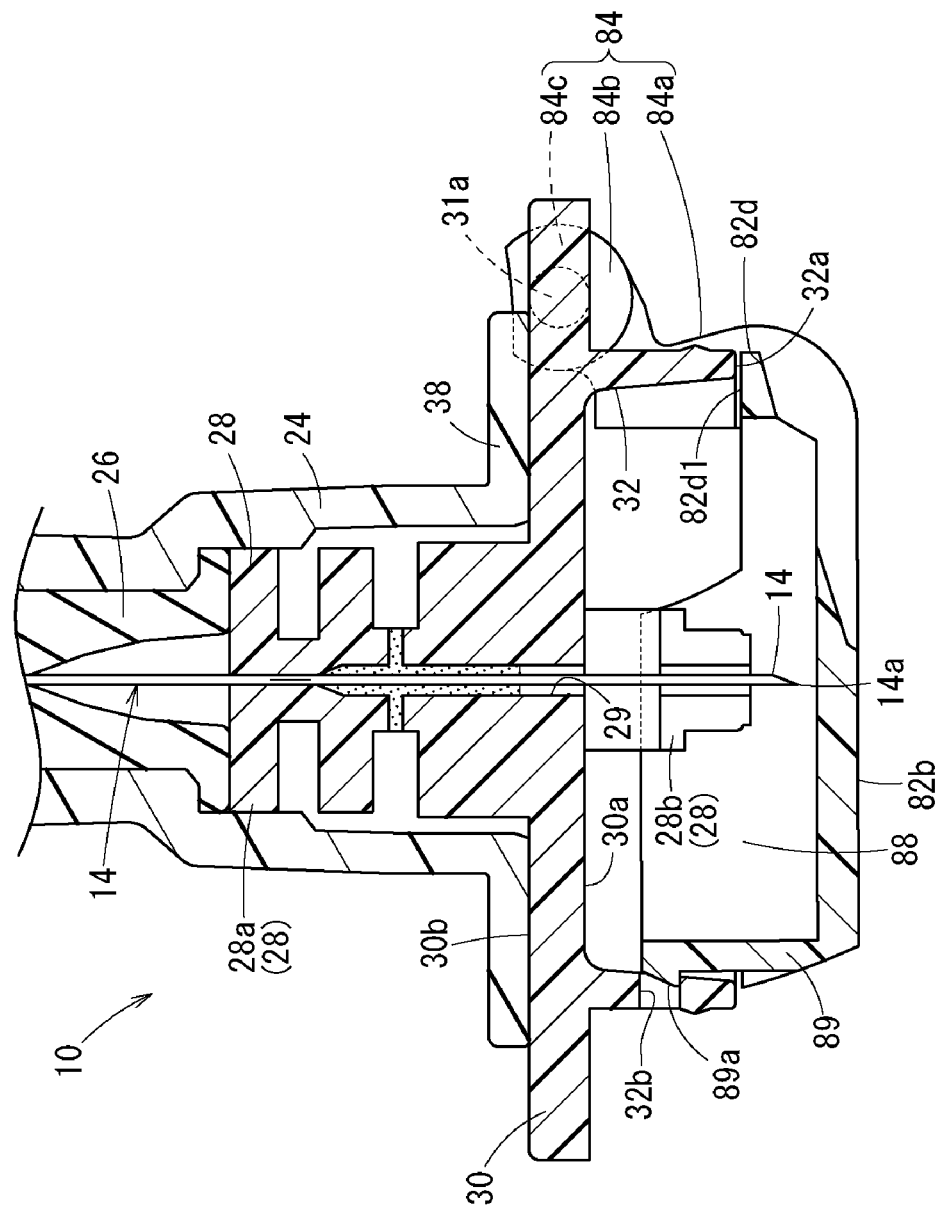
FIG. 8 is a cross-sectional view illustrating the intradermal needle illustrated in FIG. 4, with the protector held in the closed position.
Figure 9:
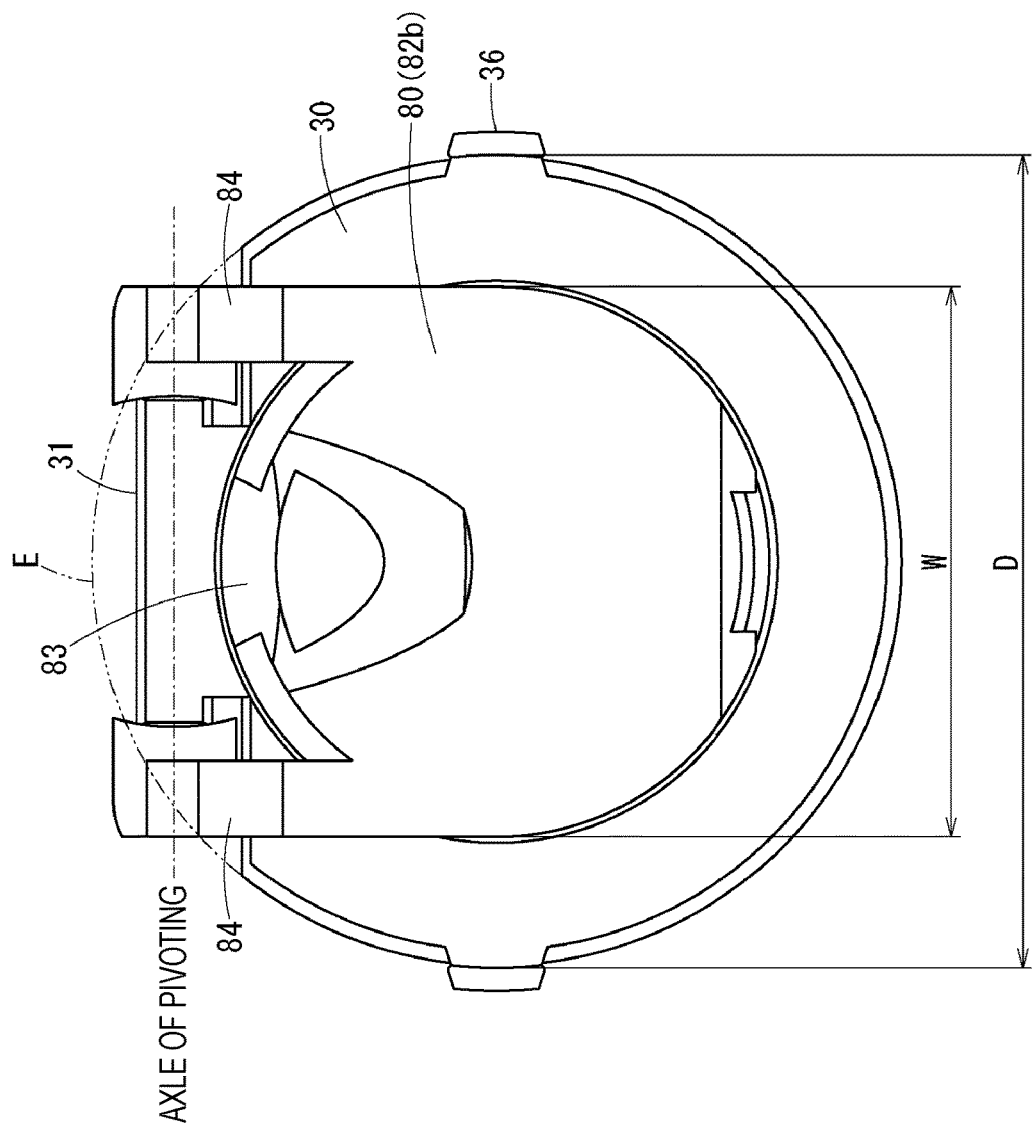
FIG. 9 is a front elevation of the intradermal needle illustrated in FIG. 8, viewed from the front end.

Next, a structure of the protector 80 provided to the intradermal needle 10 will be explained. The protector 80 is housed in the packaging article 12 while being maintained in the open position as illustrated in FIGS. 3 and 4, and is pivoted, after use of the intradermal needle 10, around the axle of pivoting (pivot axis or pivot axle) perpendicular to the axial direction of the axial part 28, to reach the closed position as illustrated in FIGS. 8 and 9, to thereby cover the needle tip 14*a*. The protector 80 has, as illustrated in FIG. 4, the lid member 82, and a protector mounting part 31 that holds the lid member 82 in a freely pivotable manner.

Now in the description below, the direction approaching the axis of the needle hub 16 is referred to as inward, inner or inside, meanwhile the direction departing from the axis of the needle hub 16 is referred to as outward, outer or outside. The lid member 82 has a lid 82*b* and arms 84.

The lid 82*b* is a plate-like member that covers the needle tip 14*a* of the tubular needle 14, when moved to the closed position (see FIG. 8). The face of the lid 82*b* opposed to the tubular needle 14, in the closed position, is referred to as an inner face 82*b*1, and the face on the opposite side is referred to as an outer face 82*b*2.

Figure 5A:
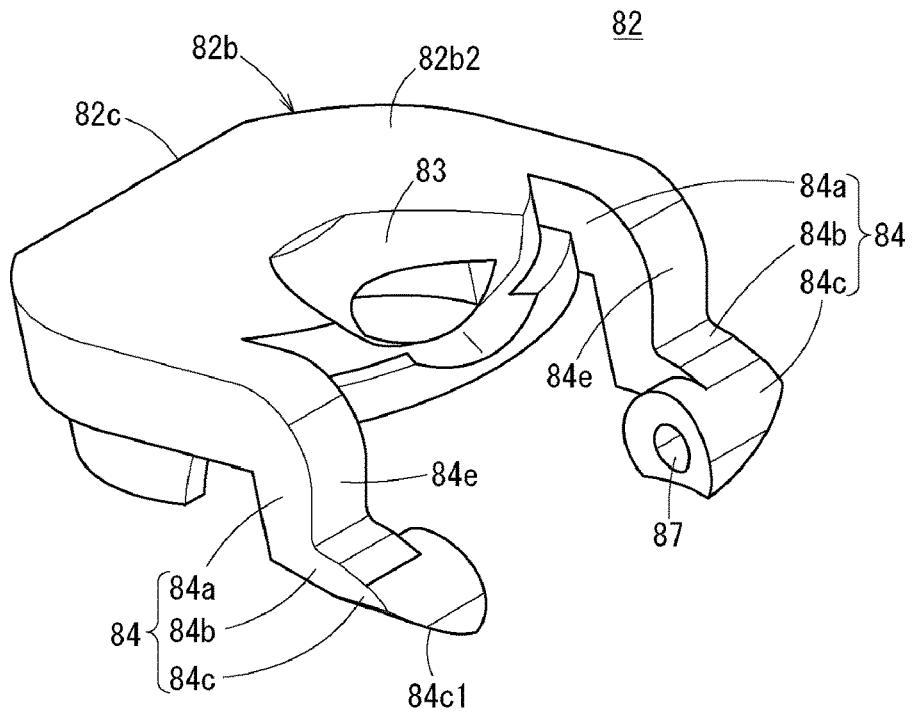
FIG. 5A is a perspective view illustrating a lid member of the protector when viewed from the exterior.

The lid 82*b* is, as illustrated in FIG. 5A, has a shape similar to the annular or ring-shaped protrusion 32, so as to cover the entire range of the annular or ring-shaped protrusion 32. The lid 82*b* has a width W (see FIG. 9) equivalent to the diameter of the annular or ring-shaped protrusion 32.

If the lid 82*b* should have the width W larger than a diameter D of the wide diameter part 30, the packaging article 12 while being sized to fit the diameter of the wide diameter part 30 would not be able to house the intradermal needle 10. The width W of the lid 82*b* is therefore preferably smaller than the diameter D of the wide diameter part 30.

As illustrated in FIG. 5A, the lid 82*b* has on the outer face 82*b*2 of the lid 82*b* and in a part closer to the pivoting axle part, a cutout 83 having a shape obliquely and curvedly cut off the outer face 82*b*2. The cutout 83 is, as illustrated in FIG. 4, a part that receives the second member 24 in the open position of the lid 82*b* and contacts the second member 24, and is formed to give a curved face conforming to the cylindrical side face of the second member 24. Although FIG. 5A illustrates the cutout 83 that partially extends through the lid 82*b* to reach the inner face 82*b*1, such through part is positioned away from the needle tip 14*a* of the tubular needle 14, without particular inconvenience for the protection of the needle tip 14*a*. With the cutout 83 provided in this way, the lid 82*b* in the open position may be arranged near the axis of the needle hub 16 and housed relatively compactly, making housing in the packaging article 12 easier.

Meanwhile, the lid 82*b* has on the free end side of the lid 82*b* (the side opposite to the axle mounting part 84*c*), an end face 82*c* that is obliquely cut. The end face 82*c* helps prevent the lid 82*b* from coming into contact with the syringe 20, when the syringe 20 is attached to the intradermal needle 10 housed in the packaging article 12. That is, the end face 82*c* of the lid 82*b* is formed to be positioned in the open position ahead of the syringe 20 to be attached, so that the lid 82*b* will not overlap the area of attachment of the syringe 20.

Figure 5B:
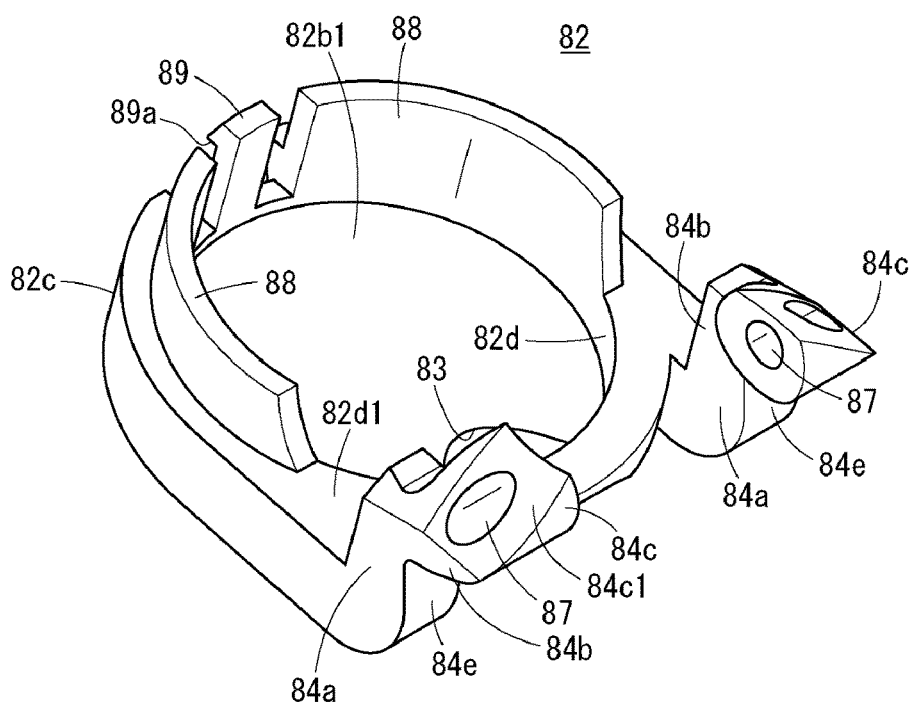
FIG. 5B is a perspective view illustrating the lid member of the protector as viewed from the interior.

As illustrated in FIG. 5B, the lid 82*b* has a wall 82*d* protruding like a wall from the circumference of the inner face 82*b*1. The wall 82*d* has an end face 82*d*1 (first face)

which serves as a face brought into contact in the closed position (see FIG. 8) with the end face 32a of the annular or ring-shaped protrusion 32. That is, the end face 82d1 of the wall 82d comes into contact with the end face 32a of the annular or ring-shaped protrusion 32 to stop pivoting of the protector 80 at the closed position of the lid 82b. Such wall 82d with the end face 82d1 constitutes the closed position restriction member.

The wall 82d has a height of protrusion measured from the inner face 82b1, equivalent to or larger than the length of protrusion of the needle tip 14a of the tubular needle 14 from the annular or ring-shaped protrusion 32. Hence, the lid 82b in the closed position can keep the inner face 82b1 spaced ahead of the annular or ring-shaped protrusion 32 in the front end direction, and can cover the needle tip 14a that protrudes ahead of the annular or ring-shaped protrusion 32.

The wall 82d has a wall-like guide piece 88 that further protrudes beyond the wall 82d on a part of the wall 82d. The guide piece 88 is formed to give a shape that is within the inner circumference of the annular or ring-shaped protrusion 32. With the guide piece 88 inserted in the closed position within the annular or ring-shaped protrusion 32, the lid 82b may be prevented from rattling.

The wall 82d also has a cutoff partially on the free end side, in which a lock piece 89 with a claw 89a is formed so as to protrude from the inner face 82b1. The lock piece 89 constitutes a lock mechanism that fixes the lid 82b in the closed position, by engaging itself in the closed position with the opening 32b (see FIG. 8) of the annular or ring-shaped protrusion 32 from inside.

The lid 82b has, as illustrated in FIG. 5A, a pair of arms 84 that extend from both ends of the lid 82b in the direction of the pivot axle. The arms 84 are formed integrally with the lid 82b. Each arm 84 has a first arm 84a that extends perpendicularly towards the inner face 82b1 of the lid 82b, a second arm 84b that extends after kinked (i.e., bent) at nearly right angles from the first arm 84a, and an axle mounting part 84c provided at the end of the second arm 84b.

The axle mounting part 84c is formed to give a cylindrical shape centered round the pivot axle, and at the center of the axle mounting part 84c has a round hole 87 that receives the axle pin 31a. The axle mounting part 84c has a cutoff face 84c1 that has been cut off obliquely as illustrated in FIG. 4. The cutoff face 84c1, when viewed with the lid 82b kept in the open position, is formed inside a circular region having the same diameter as that of the wide diameter part 30.

The second arm 84b is a part that extends from the axle mounting part 84c, and is integrally formed with the axle mounting part 84c. The second arm 84b is configured to position the first arm 84a in contact with the end face 38b of the connecting wide diameter part 38 of the second member 24, when the lid 82b moves to the open position. That is, with such second member 24 provided in this way, the lid member 82 in the open position may be arranged inside the connecting wide diameter part 38, enabling compact housing of the lid member 82 while being maintained near the axis of the needle hub 16. The length of the second arm 84b may suitably be determined depending on the thickness of the wide diameter part 30 and of the connecting wide diameter part 38.

The first arm 84a extends after kinked (i.e., bent) at nearly right angles from the second arm 84b. The first arm 84a keeps the lid 82b a predetermined distance away from the pivoting axle part (axle pin 31a), and can thereby allow the lid 82b to be housed in the open position near the needle hub 16.

The first arm 84a has an inclined face 84e that comes, in the open position, into contact with the connecting wide diameter part 38. With the inclined face 84e maintained in contact with the connecting wide diameter part 38, the lid member 82 is prevented from pivoting towards the open position, and is restricted so that the lid member 82 can no longer approach the axis of the needle hub 16. That is, the inclined face 84e constitutes the open position restriction member that restricts the position of the lid member 82 in the open position, so as to stop at a predetermined angle. The angle of the inclined face 84e is determined so that the lid member 82 in the open position will have, as illustrated in FIG. 3, its free end spaced by a predetermined distance from the second member 24 of the needle hub 16. In this way, the lid member 82 can be prevented from interfering with the syringe 20 when attached to the intradermal needle 10, thus successfully preventing the assemblage work from being interrupted.

Figure 6:
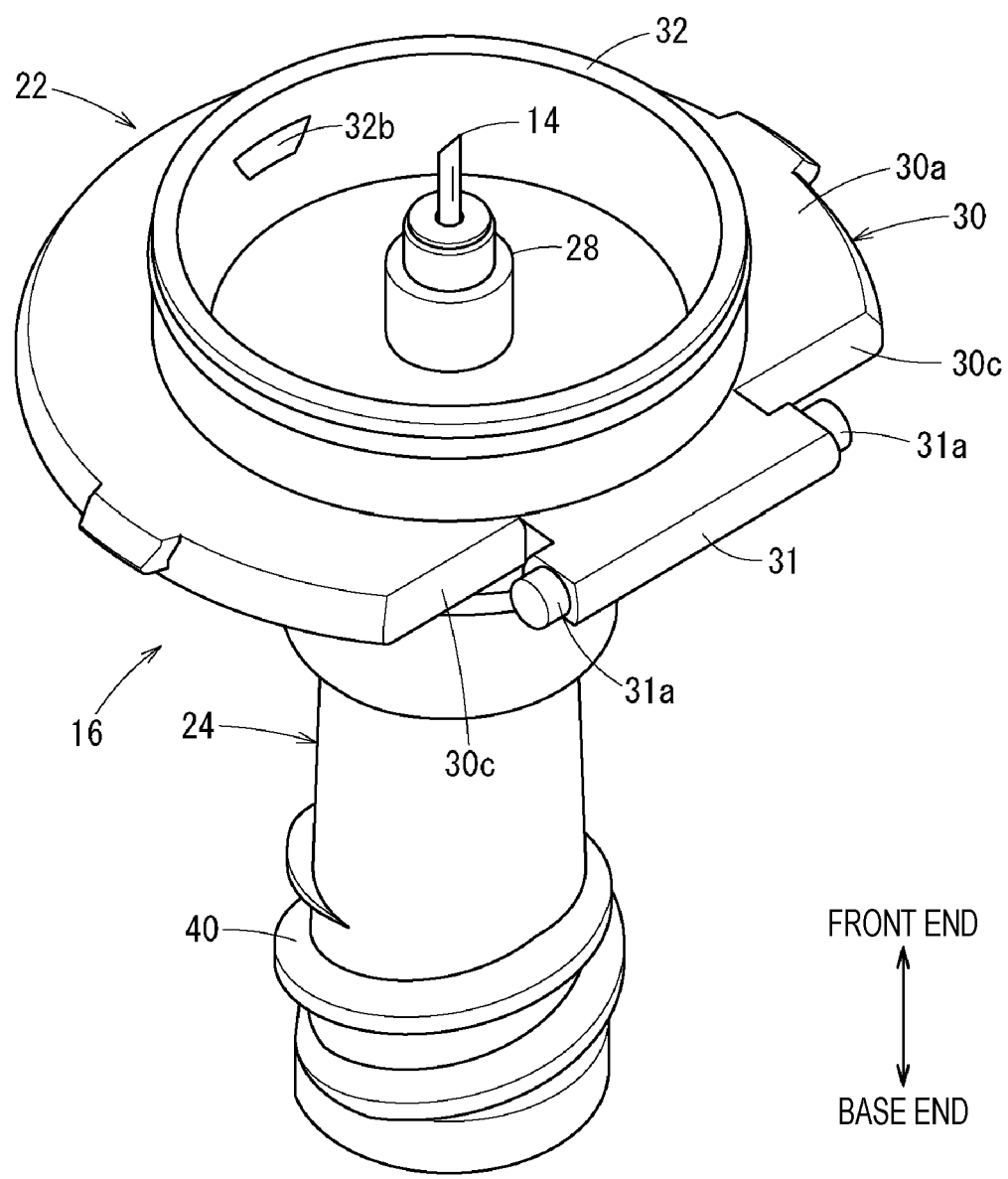
FIG. 6 is a perspective view illustrating a needle hub illustrated in FIG. 4.

As illustrated in FIG. 6, the wide diameter part 30 has on one end of the wide diameter part 30 a cutoff side 30c at which the wide diameter part 30 is straightly cut off, and a protector mounting part 31 that extends from the center of the cutoff side 30c outwards in the radial direction. The protector mounting part 31 has a T-shape when viewed from the front end, and has the axle pins 31a that extend from both sides of the protector mounting part 31. Each axle pin 31a is a member formed so as to extend in a cylindrical shape in the direction perpendicular to the axis of the needle hub 16, with the center axis of the axle pin 31a allowed to serve as the pivoting axle part (axis of rotation) of the lid member 82. As illustrated in FIG. 9, the pivoting axle part of the protector 80 is formed inside a circular region E having the diameter equal to that of the wide diameter part 30 (near the axis of the needle hub 16). With such structure, the entire part of the protector 80 including the protector mounting part 31 may be housed within the circular region E when the protector 80 is in the open position, thus enabling the housing in the small packaging article 12.

The protector 80 is manufactured by attaching the lid member 82 to the protector mounting part 31. That is, while expanding the arms 84 of the lid member 82 in the axial direction, the protector mounting part 31 is fitted in between the pair of axle mounting parts 84c. By fitting the axle pins 31a into the holes 87 of the axle mounting part 84c, the protector 80 is built up.

Figure 7:
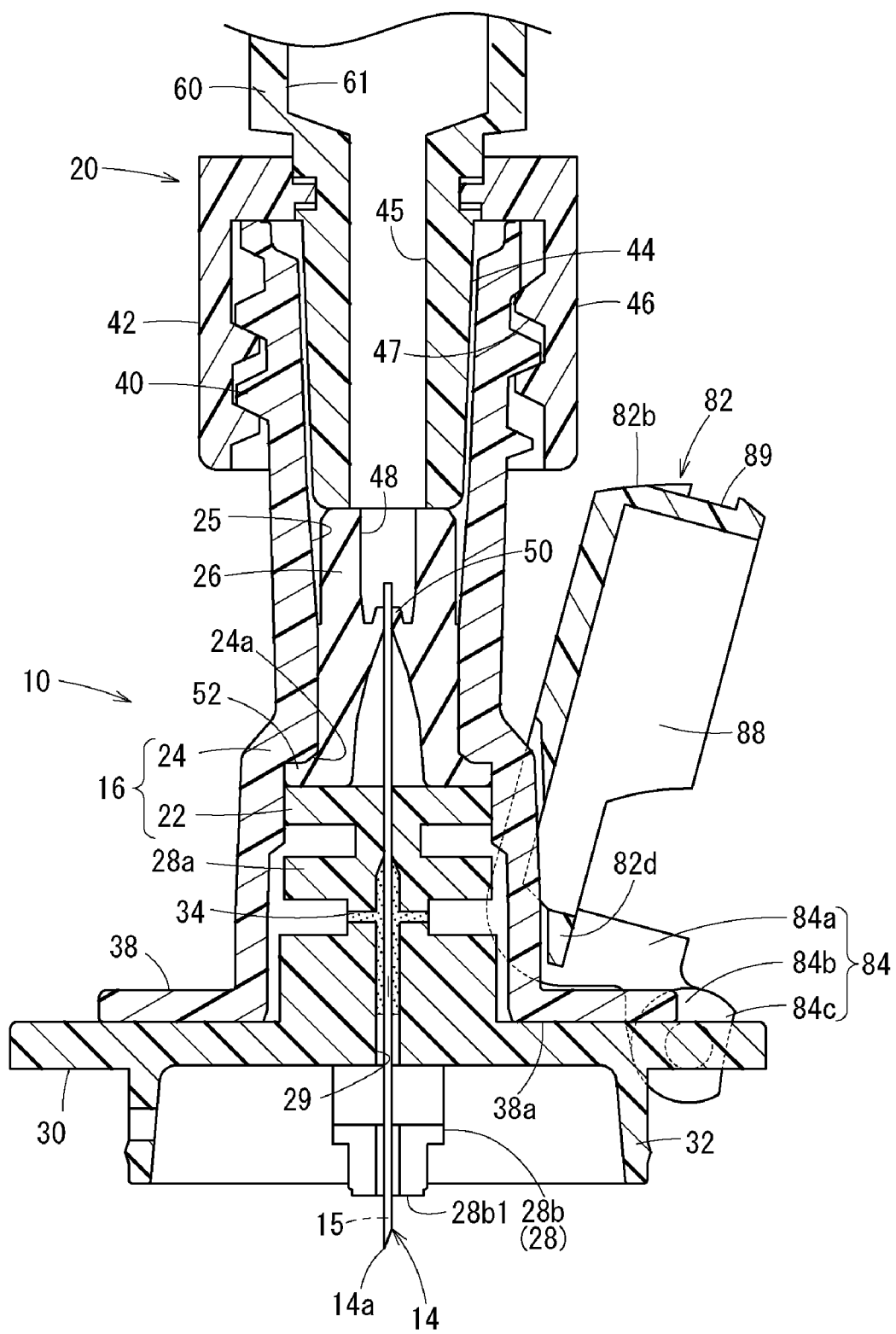
FIG. 7 is a cross-sectional view illustrating the intradermal needle illustrated in FIG. 4, with a syringe attached to the intradermal needle.

The intradermal needle 10 having the protector 80 is used with the syringe 20 attached to the intradermal needle 10 as illustrated in FIG. 7. The syringe 20 has in its front end part 42, a nozzle 44 having an ejection channel 45 communicated with a reservoir 61 of the medical solution (i.e., drug), and a connector 46 arranged around the nozzle 44, with the female screw 47 threaded on the inner face. With the male screw 40 and the female screw 47 engaged, the end face of the nozzle 44 comes into contact with, and pressurizes the base end face of the elastic member 26.

The elastic member 26 of the intradermal needle 10 is a cylindrical connection member that keeps the base end of the tubular needle 14 liquid-tight, and holds the needle hole 15 opposing to the ejection channel 45 of the nozzle 44. The elastic member 26 has a tubular needle hole 48 inside of the elastic member 26, and the tubular needle hole 48 has an inner projection 50 formed in the tube hole 48 that holds the inserted tubular needle 14 in contact with the inner projection 50. The elastic member 26 is tightly fixed while fitting itself to the inner circumference of the through-hole 25 of the second member 24, and while allowing an outward projection 52, which projects at the front end side outwards in the radial direction, to be caught between the base end face of the first member 22 and a step 24a of the second member 24.

Meanwhile, the syringe 20 of the injection device 18 is given as a prefilled syringe having the medical solution preliminarily filled in the syringe 20, as illustrated in FIG. 2. The syringe 20 has, as illustrated in FIG. 2, a syringe body 54, a plunger 56 that is inserted into the syringe body 54 in a relatively movable manner, and a holder 58 that covers the outside of the syringe body 54.

The syringe body 54 has the front end part 42 (nozzle 44 and connector 46), and a barrel 60 having a reservoir 61 that communicates with the front end part 42 and stores the medical solution. Meanwhile, the plunger 56 has a gasket 62 at the front end of the plunger 56 that is inserted liquid-tight into the reservoir 61, and has an operation part 64 on the base end of the plunger 56, which is pushed by the user of the injection device 18. Alternatively, the syringe 20 may be of a type having the gasket 62 preliminarily housed in the reservoir 61, allowing the plunger 56 to be attached to the gasket 62 when the syringe 20 is used.

The holder 58 is a cylindrical body that houses and fixes the syringe body 54, and is used for widening the injection device 18, making it more convenient for the user to grip. The holder 58 has a finger flange 66 on the base end of the holder 58, on which fingers of the user who pushes the operation part 64 of the plunger 56 are hooked. The injection device 18 may alternatively have no holder 58.

The holder 58 has, arranged on the inner wall thereof surrounding the inner space, a plurality of support pieces (not illustrated) that support the front end part of the barrel 60 of the syringe body 54. The holder 58 also has, on the outer circumference of the holder 58, a lock window 68 for locking a flange (not illustrated) provided to the base end of the syringe body 54, and the holder 58 also has at around the front end of the holder, a check window 69 through which the reservoir 61 of the syringe body 54 can be visually checked.

The intradermal needle 10, the packaging article 12 that houses the intradermal needle 10, and the injection device 18 according to this embodiment are basically composed as described above. Operations of these items will be explained below.

The intradermal needle 10 is provided while being housed in a container 70 of the packaging article 12 as illustrated in FIG. 1. As described above, the intradermal needle 10 in this state is prevented from protruding from the packaging article 12, with the pair of claws 36 of the intradermal needle 10 maintained hooked on an engagement part of the container 70. The packaging article 12 encloses the intradermal needle 10 airtight, as a result of placement of the seal member 72 onto the flange 78 of the container 70.

When using the injection device 18, the seal member 72 of the packaging article 12 is peeled off, the front end of the syringe 20 is inserted into the packaging article 12, so as to connect the base end of the intradermal needle 10 and the front end part 42 of the syringe 20. That is, as illustrated in FIG. 7, the nozzle 44 of the front end part 42 is inserted into the through-hole 25 of the second member 24, and the female screw 47 of the connector 46 is screwed on the male screw 40 of the intradermal needle 10. In this process, the protector 80 of the intradermal needle 10 is maintained in the open position, and the free end of the lid member 82 is spaced by a predetermined distance from the axis of the intradermal needle 10, so as not to interfere with the connector 46 of the syringe 20. Hence, the protector 80 will no longer interfere with the attachment of the syringe 20 to the intradermal needle 10.

After the intradermal needle 10 and the syringe 20 are connected, the syringe 20 is pulled out from the packaging article 12. In this way, the pair of claws 36 of the intradermal needle 10 are released from the packaging article 12, and thereby the intradermal needle 10 and the syringe 20 are integrally taken out from the packaging article 12.

The tubular needle 14 of the intradermal needle 10 is then punctured into the living body to inject the medical solution having been stored in the reservoir 61 of the syringe 20. After injecting the medical solution, the used intradermal needle 10 is disposed.

The user in this process pivots the protector 80 with fingers to move the protector 80 (lid member 82) to the closed position. As illustrated in FIGS. 8 and 9, as the protector 80 pivots, the guide piece 88 of the lid member 82 is inserted inside the annular or ring-shaped protrusion 32 while contacting therewith, and the lid member 82 covers the annular or ring-shaped protrusion 32. As the lid member 82 is further pushed into the base end side of the annular or ring-shaped protrusion 32, the claw 89a of the lock piece 89 hooks on the opening 32b of the annular or ring-shaped protrusion 32, to thereby lock the lid 82b in the closed position. That is, the lid member 82 is fixed on the annular or ring-shaped protrusion 32 so as not to disengage. With the protector 80 thus fixed so as to cover the needle tip 14a of the intradermal needle 10, the intradermal needle 10 can now be safely disposed.

As has been described above, with the protector 80 attached pivotably around the pivot axle provided to the wide diameter part 30, and with the lid member 82 whose width W being made smaller than the diameter D of the wide diameter part 30, the intradermal needle 10 of this embodiment can now be housed in a small packaging article 12 whose inner diameter is comparable to the diameter of the wide diameter part 30.

Also provision of the arms 84 enables compact housing of the lid 82b near the axis of the needle hub 16, when the protector 80 is in the closed position, thus improving the convenience for housing in the packaging article 12.

In addition, the inclined face 84e is provided on each arm 84, as the open position restriction member that keeps the free end of the lid 82b, in the open position, away from the male screw 40 of the intradermal needle 10. With such structure, when attaching the syringe 20 to the needle hub 16, the free end of the lid 82b may be prevented from accidentally coming into contact with the syringe 20, and from interfering attachment of the syringe 20.

The lid 82b also has the wall 82d (end face 82d1) as the closed position restriction member that restricts the stop position of the lid 82b in the closed position. With such wall 82d, the lid 82b in the closed position is kept with the inner face 82b1 of the lid 82b closer to the front end side than the annular or ring-shaped protrusion 32. This allows the lid 82b to cover the needle tip 14a from the front end side.

Also in the closed position, the lock piece 89 provided to the lid 82b engages with the opening 32b provided to the annular or ring-shaped protrusion 32, and thereby the lid member 82 is fixed to the closed position. Hence, the tubular needle 14 is prevented from being accidentally exposed, due to re-opening of the lid member 82 after moved to the closed position.

In addition, the lid 82b has, provided to a part of the lid 82b close to the pivoting axle part, the cutout 83 that houses a part of the side wall of the needle hub 16 in the open position. This consequently makes it possible to arrange the lid 82b in the open position near the axis of the needle hub 16, and to compactly house the protector 80 near the axis of the needle hub 16.

Furthermore, with the pair of arms 84 arranged away from each other in the direction of pivoting axle part of the lid 82b, the arms 84 will have enhanced rigidity at around the pivot axle, and may be prevented from deforming even under force applied from directions other than the direction around the pivot axle, so that the lid 82b may be prevented from pivoting in a wrong direction. Hence, the lid 82b will no longer pivot in a direction departing from the tubular needle 14 so as to allow the user's fingers to accidentally come into contact with the tubular needle 14. With the pair of arms 84 in this case pivotably engaged using the axle pins 31a, the strength may further be enhanced than in a case where the pivoting axle part were composed of a thin hinge.

Second Embodiment

Figure 10:
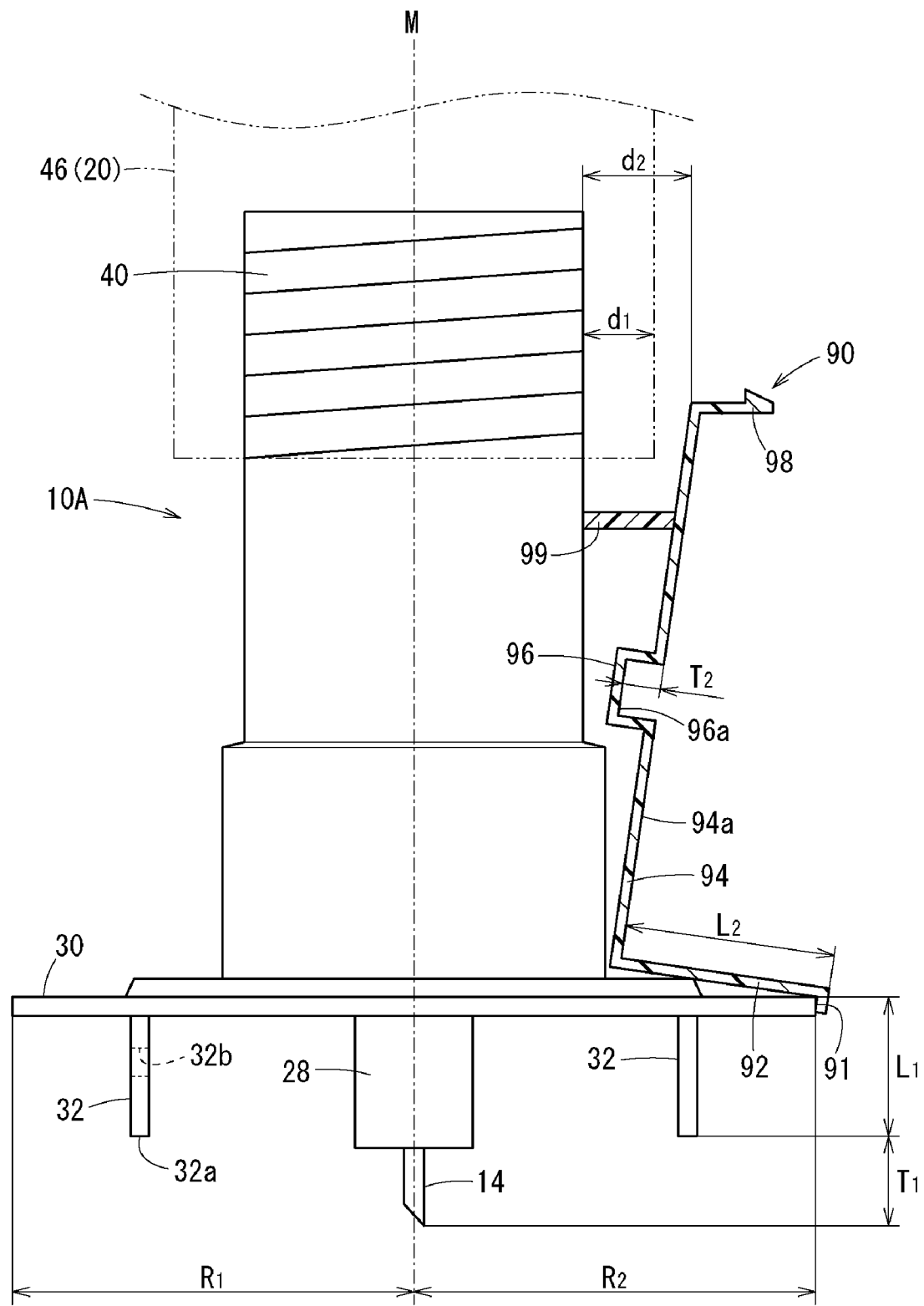
FIG. 10 is a cross-sectional view illustrating an intradermal needle according to a second embodiment.

An intradermal needle 10A of this embodiment will be explained below, referring to FIG. 10. The inner structure of the intradermal needle 10A is same as that of the intradermal needle 10 illustrated in FIG. 3, and will therefore be not explained redundantly. In the intradermal needle 10A, the same structures as those in the intradermal needle 10 having been described referring to FIGS. 1 to 9, will be given the same reference signs, and will not be detailed redundantly.

The intradermal needle 10A of this embodiment is different from the intradermal needle 10 in terms of a protector 90. The protector 90 will now be explained below. The protector 90 is formed pivotable about the wide diameter part 30 with the aid of a hinge 91 provided to the wide diameter part 30. The hinge 91 is arranged inside the wide diameter part 30 when viewed in the radial direction. That is, distance $R_2$ measured from the axis M of the intradermal needle 10A to the hinge 91 is smaller than the radius $R_1$ of the wide diameter part 30. The hinge 91, although illustrated as being thinner than the other part, is not restricted thereto. For example, the hinge 91 may have the axle pins 31a and the axle mounting parts 84c as illustrated in FIGS. 3 and 4. The protector 90 is made pivotable while being centered around the hinge 91 and on an axis perpendicular to the axis M of the intradermal needle 10A (in a direction perpendicular to a sheet of this drawing).

An arm 92 extends from the hinge 91. From the arm 92, the lid 94 extends after kinked (i.e., bent) near-vertically, and the lid 94 includes on its free end a lock piece 98 which locks to the opening 32b of the annular or ring-shaped protrusion 32. The lid 94 includes a projection 96 at the center of the lid 94, which opposes, in the closed position, to the tubular needle 14.

The arm 92 is a member that keeps the hinge 91 and an inner face 94a of the lid 94 apart, where length L2 given by the arm 92 between the pivoting axle part of the hinge 91 and the lid 94 is set nearly equal to distance $L_1$, in the axial direction of the intradermal needle 10A, between the hinge 91 and the end face of the annular or ring-shaped protrusion 32. The inner face 94a of the lid 94 comes into contact with the end face 32a of the annular or ring-shaped protrusion 32, when the protector 90 is pivoted to the closed position.

The lid 94 may have any shape so long as the center projection 96 can face an inner face 96a of the lid 94 to the tubular needle 14, when the protector 90 is pivoted to the closed position. The lid 94 is sized so as to fall, in the illustrated open position, inside a region with radius $R_1$ centered round the axis M of the intradermal needle 10A, which enables housing in the small packaging article 12 (see FIG. 1).

Distance $T_2$ between the inner face 96a of the projection 96 and the inner face 94a of the lid 94 is larger than length of protrusion $T_1$, measured from the end face of the annular or ring-shaped protrusion 32, of the tubular needle 14, and thereby the projection 96 can cover the tubular needle 14.

In the protector 90 of this embodiment, there is provided a restriction piece 99 that extends from the side wall of the intradermal needle 10A, as an open position restriction member that stops the protector 90 in the open position so as to keep the free end of the protector 90 away from the axis of the intradermal needle 10A. With the restriction piece 99 brought into contact with the lid 94, the protector 90 may be kept a predetermined distance $d_2$ away from the axis of the intradermal needle 10A. The distance $d_2$ is preferably set larger than thickness $d_1$ of the connector 46 of the syringe 20.

Also with the aforementioned intradermal needle 10A of this embodiment, convenience for housing in the small packaging article 12 can be improved.

Third Embodiment

An intradermal needle 10B of the third embodiment will be explained below, referring to FIGS. 11 to 15B. The inner structure of the intradermal needle 10B (see FIG. 13A) is same as that of the intradermal needle 10 illustrated in FIG. 3, and will therefore be not explained redundantly. In the intradermal needle 10B, the same structures as those in the intradermal needle 10 having been described referring to FIGS. 1 to 9, will be given the same reference signs, and will not be detailed redundantly.

Figure 11:
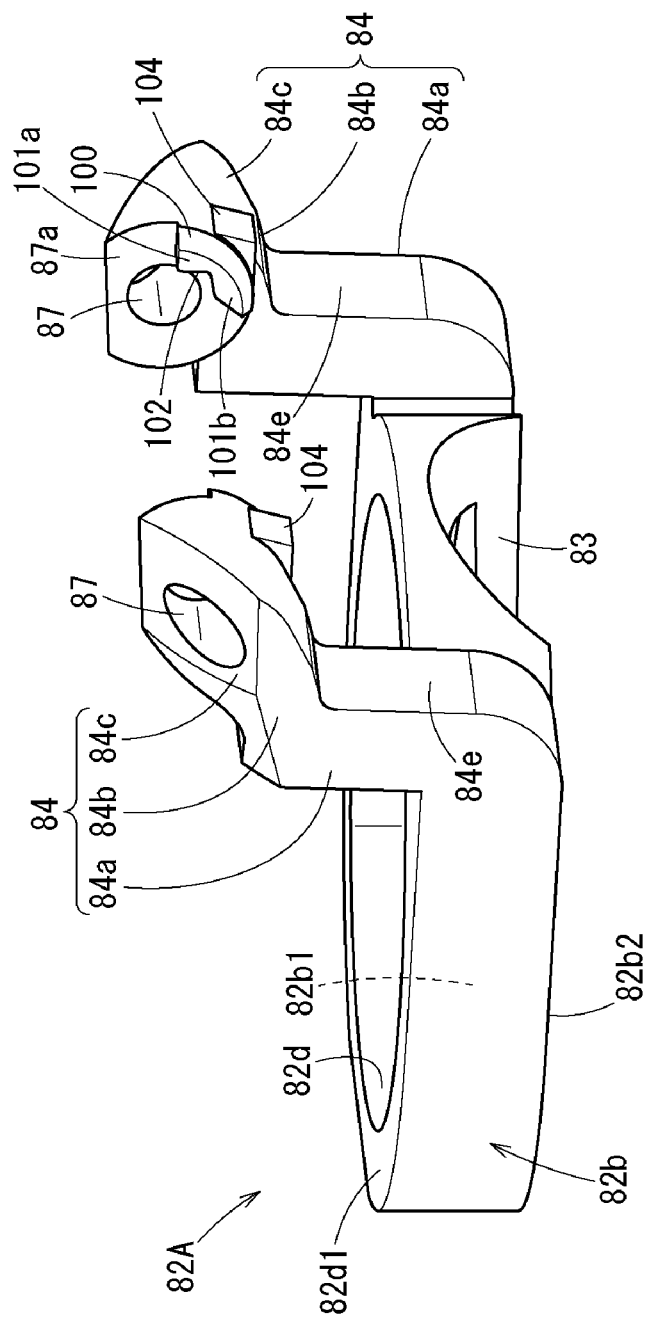
FIG. 11 is a perspective view illustrating a lid member composing a protector of an intradermal needle according to a third embodiment.
Figure 12:
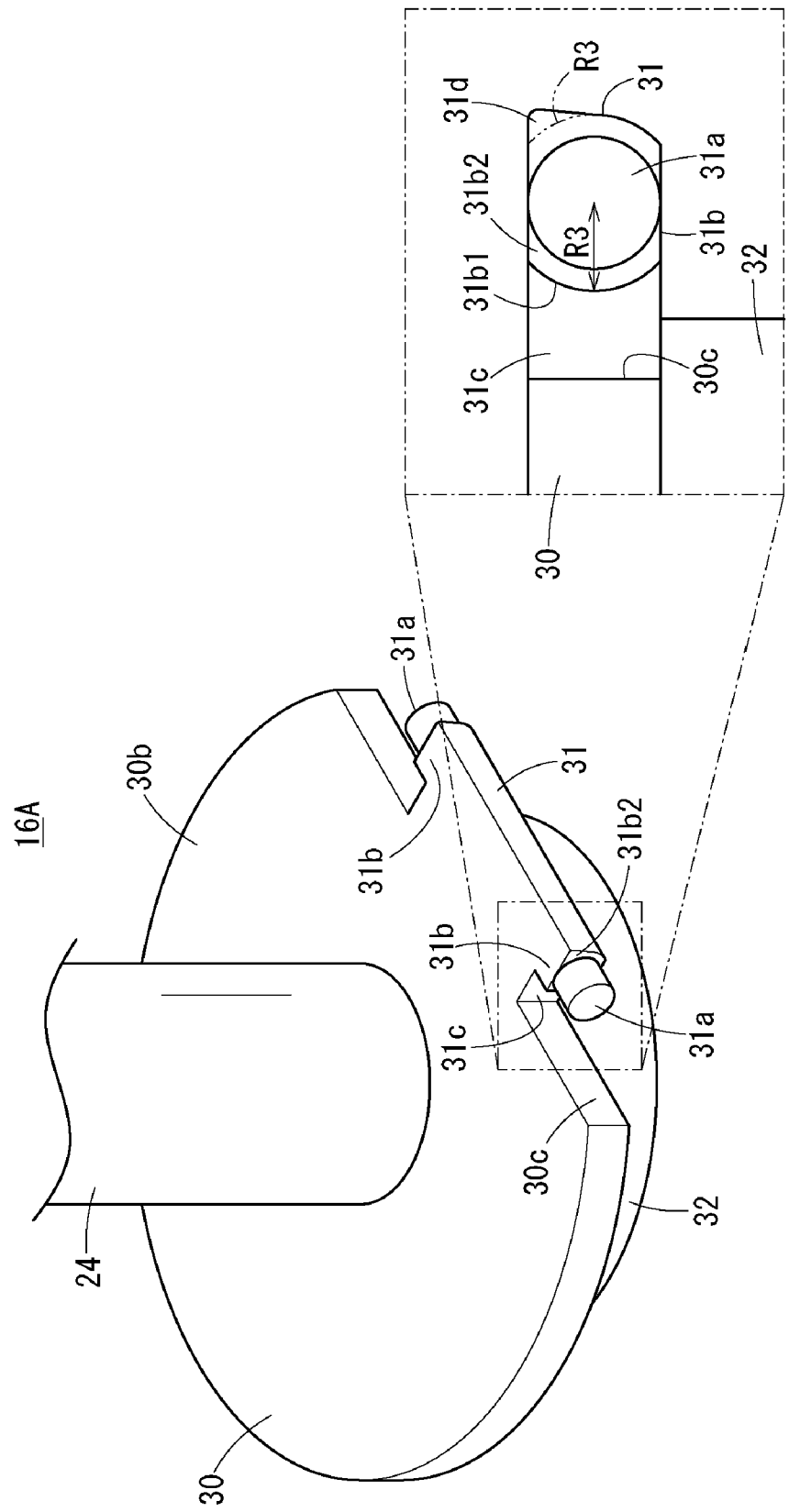
FIG. 12 is a perspective view illustrating a needle hub of the intradermal needle according to the third embodiment.

The protector 80A of this embodiment (see FIG. 13A) is built up by mounting the lid member 82A illustrated in FIG. 11 to the protector mounting part 31 illustrated in FIG. 12. The lid member 82A of this embodiment is different from the lid member 82 illustrated in FIG. 5A, in that the axle mounting parts 84c include intermediate lock pieces 100 and open position lock pieces 104, aiming at producing resistive force during pivoting to enhance safety.

As illustrated in FIG. 11, each axle mounting part 84c has the hole 87 into which each axle pin 31a of the protector mounting part 31 is inserted. Each axle mounting part 84c is built up so as to slide against the protector mounting part 31 (see FIG. 12), on a sliding face 87a which resides in the outer circumference of the hole 87 and faces to the opposing arm 84. In this embodiment, the intermediate lock piece 100 is formed on a circumferential part of the sliding face 87a, so as to protrude towards the opposing arm 84.

Each intermediate lock piece 100 has a first projection 101a and a second projection 101b that protrude towards the axial center of each hole 87, and an engagement recess 102 formed in between. The first projection 101a and the second projection 101b are formed away from each other in the circumferential direction of the hole 87. The first projection 101a and the second projection 101b are parts that reside more closely to the axial center of the hole 87 than the engagement recess 102. The first projection 101a and the second projection 101b have their ends on the center side, which are approximately a length equivalent to radius $R_3$ away from the axis of the hole 87, so as not to interfere with axle supports 31b (see FIG. 12) formed at the bases of the axle pins 31a, when the lid member 82A pivots.

Figure 13A:
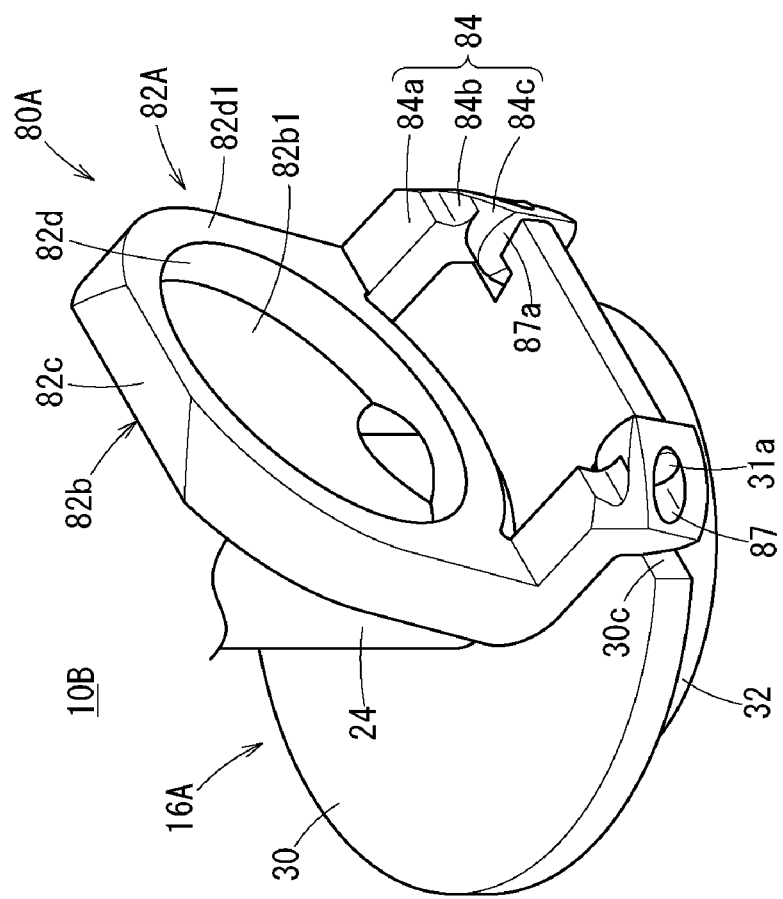
FIG. 13A is a perspective view illustrating the intradermal needle according to the third embodiment with the protector held in the open position.

Each intermediate lock piece 100 may be at any position not specifically limited in the circumferential direction of the hole 87, but may preferably be at a position where the lid member 82A can produce resistive force against pivoting, when the lid member 82A is pivoted ahead of the wide diameter part 30 (see FIG. 13A).

The open position lock piece 104 is formed so as to protrude outward in the radial direction from the outer circumference of the axle mounting part 84c that is formed cylindrically around the hole 87. The open position lock piece 104 extends in the direction the second arm 84b extends, and is built so as to restrict pivoting of the lid member 82A when the lid member 82A is kept in the open position, while allowing itself to contact with the cutoff side 30c of the wide diameter part 30 (see FIG. 12).

The lid member 82A of this embodiment does not have the guide piece 88 (see FIG. 5B) that protrudes from the wall 82d, and is built to cover the annular or ring-shaped protrusion 32 solely with the wall 82d. Note however that the lid member 82A is not limited thereto, instead allowing provision of the guide piece 88.

As illustrated in FIG. 12, the needle hub 16A of this embodiment has a cutoff side 30c formed so as to straightly cut off the wide diameter part 30 at one end of the needle hub 16A, and a protector mounting part 31 that extends from the center of the cutoff side 30c outwards in the radial direction. The protector mounting part 31 has a T-shape when viewed from the front end, and has the axle pins 31a that extend from both sides of the protector mounting part 31. Each axle pin 31a is a member formed so as to extend in a cylindrical shape in the direction perpendicular to the axis of the needle hub 16A, with the center axis of each axle pin 31a allowed to serve as the pivoting axle part (axis of rotation) of the lid member 82A.

On the base end side of the axle pins 31a of the protector mounting part 31, there are provided the axle supports 31b that support the axle pins 31a, which are formed so as to extend in the axial direction of the axle pins 31a. The axle supports 31b are formed so as to expand in the radial direction of the axle pins 31a, and have steps 31b2 that are composed of end faces perpendicular to the axis of the axle pins 31a, between themselves and the axle pins 31a. The steps 31b2 constitute faces against which the sliding face 87a of the lid member 82A can slide. Between the axle supports 31b and the cutoff side 30c, there are formed recesses 31c that allow insertion of the axle mounting part 84c.

As illustrated in a partially enlarged view in FIG. 12, the axle support 31b has a side face which is composed of an arcuate curved face 31b1 formed so as to extend along the range given by a length equivalent to radius $R_3$ from the axis of the axle pin 31a. Hence the curved face 31b1 will no longer interfere with the intermediate lock piece 100 of the axle mounting part 84c. Meanwhile, the axle support 31b has, formed at the corner on the side closer to the base end face 30b, a pivoting restriction projection 31d that protrudes beyond the range given by a length equivalent to radius $R_3$ from the axis of the axle pin 31a. The pivoting restriction projection 31d is built to come into contact with the intermediate lock piece 100 to thereby produce resistive force against pivoting of the lid member 82A.

Operations of the intradermal needle 10B of this embodiment will be explained below.

As illustrated in FIG. 13A, the protector 80A of the intradermal needle 10B of this embodiment is built by engaging the pair of holes 87 of the lid member 82A with the axle pins 31a of the protector mounting part 31.

Figure 13B:
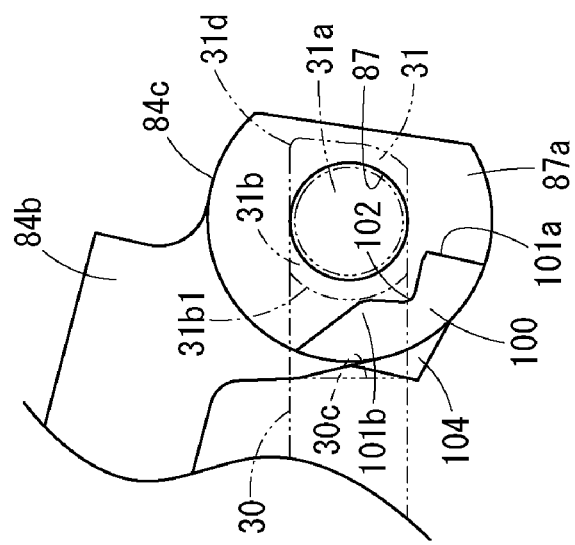
FIG. 13B is an explanatory drawing illustrating a positional relation between the lid member and a protector mounting part in the state illustrated in FIG. 13A.

As illustrated in FIG. 13B, with the lid member 82A held in the open position, the open position lock piece 104 comes into contact with the cutoff side 30c that protrudes from the outer circumference of the axle mounting part 84c. Hence, the force of pivoting the lid member 82A clockwise from the illustrated position towards the closure, will be resisted by contact of the open position lock piece 104 with the cutoff side 30c. The lid member 82A may therefore be prevented from rattling during carriage or usage of the intradermal needle 10B, and from unintentional closure.

Note that if the user applies a predetermined level or larger force through its finger to pivot the lid member 82A towards the closure, the lid member 82A may be closed despite the resistive force produced by the open position lock piece 104 and the cutoff side 30c. Upon disengagement of the open position lock piece 104 from the cutoff side 30c, the lid member 82A pivots rather smoothly.

Figure 14B:
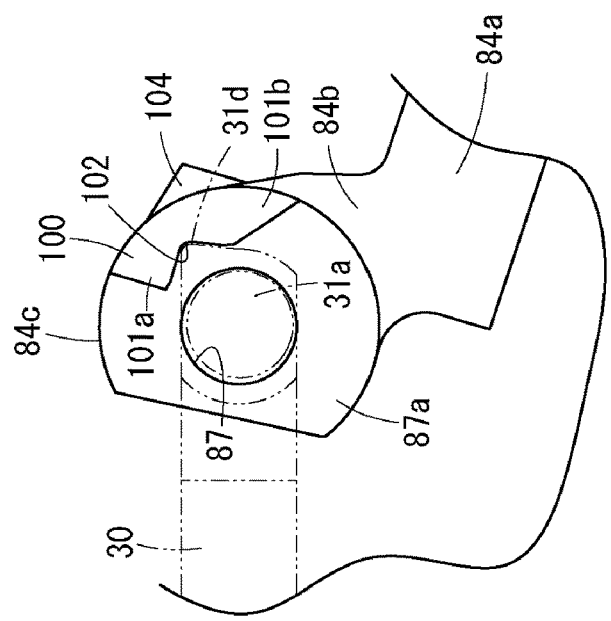
FIG. 14B is an explanatory drawing illustrating a positional relation between the lid member and the protector mounting part in the state illustrated in FIG. 14A.
Figure 14A:
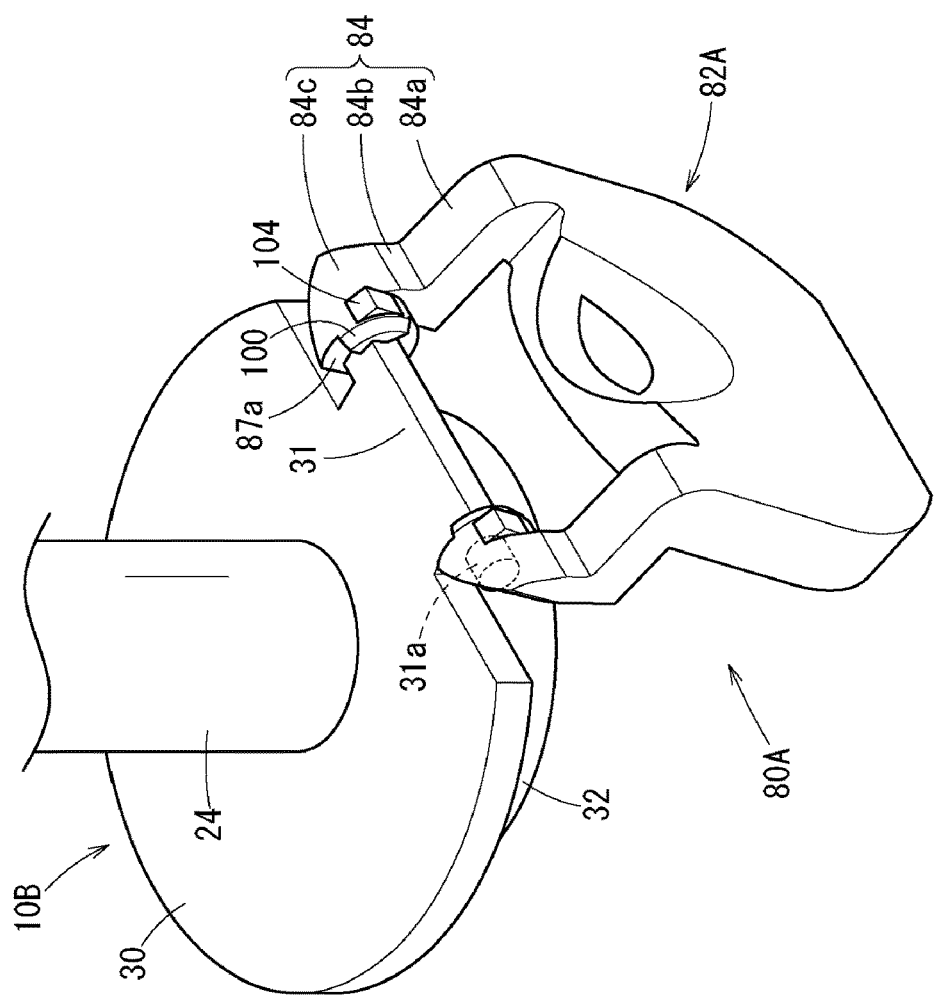
FIG. 14A is a perspective view illustrating the intradermal needle illustrated in FIG. 13A with the protector held at an intermediate position.

During pivoting of the lid member 82A towards the closure, the lid member 82A is temporarily restricted from pivoting in the middle way as illustrated in FIG. 14A. Pivoting of the lid member 82A in this process is restricted by resistive force, as a result of interference between the first projection 101a or the second projection 101b of the intermediate lock piece 100, with the pivoting restriction projection 31d of the axle support 31b as illustrated in FIG. 14B. Upon fitting of the pivoting restriction projection 31d into the engagement recess 102 of the intermediate lock piece 100, the lid member 82A stops pivoting. Upon such temporary stopping of pivoting of the lid member 82A at an intermediate position near the closed position, the lid member 82A can be prevented from being slammed close, and thereby the user can be prevented from erroneous handling and erroneous puncture. That is, by virtue of the temporary resistance against pivoting of the lid member 82A, the user will become cautious to move the lid member 82A towards the closed position, and can prevent erroneous puncture.

Upon further pivoting of the lid member 82A from the intermediate position towards the closure, the intermediate lock piece 100 is disengaged from the pivoting restriction projection 31d as illustrated in FIG. 15B. Then the lid member 82A moves to the closed position as illustrated in FIG. 15A, to thereby stop pivoting. With the needle tip 14a thus covered with the lid member 82A, the intradermal needle 10B now can be safely disposed.

The intradermal needle 10B of this embodiment can exhibit effects below.

The intradermal needle 10B of this embodiment has the open position lock piece 104 and the intermediate lock piece 100 that restrict pivoting of the lid member 82A. The open position lock piece 104 is formed so as to protrude outwards in the radial direction from the outer circumference of the axle mounting part 84c, and is designed to restrict pivoting of the lid member 82A, when the lid member 82A is held in the open position near the axis of the needle hub 16A, and comes into contact with the cutoff side 30c. This can successfully prevent accidental closure of the lid member 82A, during carriage or usage of the intradermal needle 10B.

In the intradermal needle 10B, the intermediate lock piece 100 is formed so as to protrude from the sliding face 87a of the axle mounting part 84c, and is designed to produce resistive force before the lid member 82A reaches the closed position, as a result of interference with the pivoting restriction projection 31d of the protector mounting part 31. This temporarily slows down pivoting of the lid member 82A, giving the user a chance to be careful, and to avoid erroneous puncture.

Although having described this invention referring to the preferred embodiments, this invention is not limited to these embodiments, and may of course be modified in various ways without departing from the spirit of this invention. For example, the syringe 20 may be of a type filled with a medical solution immediately before use, rather than the prefilled syringe.

The detailed description above describes embodiments of an intradermal needle used for injecting drug into living body, a packaging article of the intradermal needle, and an injection device. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An intradermal needle comprising:
    a tubular needle including a needle tip configured to puncture a living body;
    a needle hub configured to support the tubular needle;
    a flange fixed to and extending outwardly from the needle hub so that the flange is an enlarged diameter part of the needle hub;
    an annular protrusion extending to a front end side of the enlarged diameter part of the needle hub, and wherein the annular protrusion has a cylindrical shape that surrounds a periphery of the tubular needle;
    a protector pivotably attached to the enlarged diameter part of the needle hub, the protector configured to be movable from an open position in which the needle tip is exposed and uncovered by the protector to a closed position in which the needle tip is covered by the protector, the protector being pivotably mounted on a pivoting axle part arranged within a circular region having a same diameter as a diameter of the enlarged diameter part of the needle hub;
    wherein the protector includes a lid having a width smaller than an outer diameter of the enlarged diameter part of the needle hub and the protector in the open position is within an imaginary cylindrical region having a diameter equal to the outer diameter of the enlarged diameter part of the needle hub; and
    a cutout that houses a part of the needle hub in the open position.

2. The intradermal needle according to claim 1, further comprising:
    a pair of arms that are spaced apart from each other in an axial direction of the pivoting axle part, each of the pair of arms includes a first arm that extends perpendicularly towards an inner face of the lid and being pivotably supported by the pivoting axle part, the pair of arms being configured to maintain the lid in the open position away from the pivoting axle part and near the axis of the needle hub; and
    each of the first arm of the pair of arms including an inclined face configured to maintain a free end of the lid in the open position and away from the needle hub.

3. The intradermal needle according to claim 2, wherein the pivoting axle part has a pair of axle pins spaced apart in the axial direction, and the pair of arms are engaged with the axle pins in a freely pivotable manner.

4. The intradermal needle according to claim 2, wherein each of the pair of arms includes a second arm that is bent and extends from the first arm, and an axle mounting part provided at an end of the second arm.

5. The intradermal needle according to claim 1, wherein the lid has a wall configured to restrict a stop position of the lid at the closed position of the protector, and the wall maintains the inner face of the lid, facing to the needle tip, closer to the front end side than the annular protrusion.

6. The intradermal needle according to claim 5, further comprising:
    a claw on the wall of the lid configured to hold the lid in the closed position.

7. The intradermal needle according to claim 1, wherein the needle hub possesses a central axis extending through the needle hub, the needle hub including a front end side and a base end side on opposite axial sides of the needle hub.

8. The intradermal needle according to claim 1, wherein the lid is an annular plate that covers the needle tip of the tubular needle, and when moved to the closed position, the lid covers an entirety of the annular protrusion.

9. A packaging article comprising:
    an intradermal needle; and
    a container in which is positioned the intradermal needle, the intradermal needle including a tubular needle having a needle tip configured to puncture a living body, a needle hub supporting the tubular needle, a flange fixed to and extending outwardly from the needle hub so that the flange is an enlarged diameter part of the needle hub, an annular protrusion extending to a front end side of the enlarged diameter part of the needle hub, and wherein the annular protrusion has a cylindrical shape that surrounds a periphery of the tubular needle, a protector pivotably attached to the enlarged diameter part of the needle hub, the protector configured to be movable from an open position in which the needle tip is exposed and uncovered by the protector to a closed position in which the needle tip is covered by the protector, the protector being pivotably mounted on a pivoting axle part arranged within a circular region having a same diameter as a diameter of the enlarged diameter part of the needle hub and centered around an axis of the needle hub, the protector including a lid having a width smaller than an outer diameter of the enlarged diameter part of the needle hub and a pair of arms that are spaced apart from each other in an axial direction of the pivoting axle part, each of the pair of arms includes a first arm that extends perpendicularly towards an inner face of the lid and being pivotably supported by the pivoting axle part, the pair of arms being configured to maintain the lid in the open position away from the pivoting axle part and near an axis of the needle hub, and wherein the protector in the open position is within an imaginary cylindrical region having a diameter equal to the outer diameter of the enlarged diameter part of the needle hub; and
    the container having an inner diameter nearly equal to the outer diameter of the enlarged diameter part of the needle hub, and the intradermal needle being positioned in the container with the protector in the open position.

10. The packaging article according to claim 9, further comprising:
    each of the first arm of the pair of arms including an inclined face configured to maintain a free end of the lid in the open position and away from the needle hub.

11. The packaging article according to claim 9, wherein the lid has a wall configured to restrict a stop position of the lid at the closed position of the protector, and the wall maintains an inner face of the lid, facing to the needle tip, closer to the front end side than the annular protrusion.

12. The packaging article according to claim 11, further comprising:

a claw on the wall of the lid configured to hold the lid in the closed position.

13. The packaging article according to claim 9, further comprising:
a cutout configured to house a part of the needle hub in the open position, the cutout being located closer to the pivoting axle part of the lid than the axis of the needle hub.

14. The packaging article according to claim 9, wherein the pivoting axle part has a pair of axle pins spaced apart in the axial direction, and the arms are engaged with the axle pins in a freely pivotable manner.

15. The packaging article according to claim 9, wherein the needle hub possesses a central axis extending through the needle hub, the needle hub including a front end side and a base end side on opposite axial sides of the needle hub.

16. An injection device comprising:
an intradermal needle;
a syringe attached to the intradermal needle in a detachable manner; and
the intradermal needle including a tubular needle having a needle tip configured to puncture a living body, a needle hub supporting the tubular needle, a flange fixed to and extending outwardly from the needle hub so that the flange is an enlarged diameter part of the needle hub, an annular protrusion extending to a front end side of the enlarged diameter part of the needle hub, and wherein the annular protrusion has a cylindrical shape that surrounds a periphery of the tubular needle, and a protector pivotably attached to the enlarged diameter part of the needle hub, the protector configured to be movable from an open position in which the needle tip is exposed and uncovered by the protector to a closed position in which the annular protrusion and the tubular needle is covered by the protector, the protector being mounted on a pivoting axle part arranged within a circular region having a same diameter as an outer diameter of the enlarged diameter part of the needle hub and centered around an axis of the needle hub, the protector including a lid having a width smaller than the outer diameter of the enlarged diameter part of the needle hub and a pair of arms that are spaced apart from each other in an axial direction of the pivoting axle part, each of the pair of arms includes a first arm that extends perpendicularly towards an inner face of the lid and being pivotably supported by the pivoting axle part, the pair of arms being configured to maintain the lid in the open position away from the pivoting axle part and near an axis of the needle hub, and wherein the protector in the open position is within an imaginary cylindrical region having a diameter equal to the outer diameter of the enlarged diameter part of the needle hub.

17. The injection device according to claim 16, further comprising:
each of the first arm of the pair of arms including an inclined face configured to maintain a free end of the lid in the open position and away from the needle hub; and
wherein the lid has a wall configured to restrict a stop position of the lid at the closed position of the protector, and the wall maintains an inner face of the lid, facing to the needle tip, closer to the front end side than the annular protrusion.

18. The injection device according to claim 17, further comprising:
a claw on the wall of the lid configured to hold the lid in the closed position; and
a cutout configured to house a part of the needle hub in the open position, the cutout being located closer to the pivoting axle part of the lid than the axis of the needle hub.

19. The injection device according to claim 18, wherein the pivoting axle part includes a pair of axle pins spaced apart in the axial direction, and the pair of arms are engaged with the axle pins in a freely pivotable manner.

* * * * *